United States Patent
Lukyanov et al.

(10) Patent No.: US 8,481,307 B2
(45) Date of Patent: Jul. 9, 2013

(54) MODIFIED FLUORESCENT PROTEINS AND METHODS FOR USING SAME

(75) Inventors: Sergey A. Lukyanov, Moscow (RU); Dimitry M. Chudakov, Moscow (RU)

(73) Assignee: Evrogen JSC (RU)

( * ) Notice: Subject to any disclaimer, the term of this patent is extended or adjusted under 35 U.S.C. 154(b) by 79 days.

(21) Appl. No.: 13/203,964

(22) PCT Filed: May 10, 2010

(86) PCT No.: PCT/IB2010/001327
§ 371 (c)(1), (2), (4) Date: Nov. 14, 2011

(87) PCT Pub. No.: WO2010/131115
PCT Pub. Date: Nov. 18, 2010

(65) Prior Publication Data
US 2012/0094377 A1    Apr. 19, 2012

Related U.S. Application Data

(60) Provisional application No. 61/215,912, filed on May 11, 2009.

(51) Int. Cl.
*C12N 15/00*    (2006.01)
*C12N 1/20*    (2006.01)
*C07H 21/02*    (2006.01)

(52) U.S. Cl.
USPC ............. 435/320.1; 435/252.3; 435/325; 536/23.1

(58) Field of Classification Search
USPC ............ 536/23.1; 530/350; 435/320.1, 252.3, 435/325
See application file for complete search history.

(56) References Cited

U.S. PATENT DOCUMENTS 7,638,615 B1 * 12/2009 Lukyanov et al. ............ 536/23.1
7,972,834 B2 * 7/2011 Lukyanov et al. .......... 435/252.3
8,138,320 B2 * 3/2012 Lukyanov et al. ............ 536/23.1

FOREIGN PATENT DOCUMENTS

WO    2007085923    8/2007

OTHER PUBLICATIONS

Shaner et al., "Improving the photostability of bright monomeric orange and red fluorescent proteins"; Nat. Methods (2008) No. 6., vol. 5; pp. 545-551.
Shcherbo et al., "Far-red fluorescent tags for protein imaging in living tissues" J. Biochem (2009) vol. 418, No. 3; pp. 567-574.

* cited by examiner

*Primary Examiner* — Karen Cochrane Carlson

(57) ABSTRACT

Nucleic acid molecules encoding improved fluorescent mutants of the mKate2 protein, variants and derivatives thereof are provided, as well as proteins and peptides encoded by these nucleic acids. Also provided are proteins that are substantially similar to, or derivatives, homologues, or mutants of, the above-referenced specific proteins. Also provided are fragments of the nucleic acids and the peptides encoded thereby, as well as antibodies specific to the proteins and peptides of the invention. In addition, host-cells, stable cell lines and transgenic organisms comprising above-referenced nucleic acid molecules are provided. The subject protein and nucleic acid compositions find use in a variety of different applications and methods, particularly for labeling of biomolecules, cells or cell organelles. Finally, kits for use in such methods and applications are provided.

17 Claims, 4 Drawing Sheets

```
                                     [    *         20         *         40
mKate2   (SEQ ID NO:2)   : M◼--◼L◼◼◼MH◼◼L◼M◼G◼VN◼H◼F◼C◼◼EGEG◼◼◼◼G : 38
mKate2M1 (SEQ ID NO:4)   : M◼--◼L◼◼◼MH◼◼L◼M◼G◼VN◼H◼F◼C◼◼EGEG◼◼◼◼G : 38
mKate2.5 (SEQ ID NO:28)  : M◼--◼L◼◼◼MH◼◼L◼M◼G◼VN◼H◼F◼C◼◼EGEG◼◼◼◼G : 38
mKate2.7C(SEQ ID NO:30)  : M◼--◼L◼◼◼MP◼◼L◼M◼G◼VN◼H◼F◼C◼◼EGEG◼◼◼◼G : 38
DsRed2   (SEQ ID NO:37)  : MA◼SENV◼T◼FMRF◼VRM◼G◼VNGHEFEIEGEGEG◼◼◼◼G : 40
avGFP    (SEQ ID NO:36)  : MSKGE◼LFTGVVP◼LVELDGDVNGHKFSV◼GEGEGDATYG : 40
                           M  s   e6i e 6   k6 6eGtVN H F    EGEG pyeG

*         60        +++  *         80
mKate2   (SEQ ID NO:2)   : ◼◼TMR◼◼AV◼G◼◼LP◼◼F◼◼LA◼◼FMYG◼◼◼F◼N◼TQG◼ : 78
mKate2M1 (SEQ ID NO:4)   : ◼◼TMR◼◼AV◼G◼◼LP◼◼F◼◼LA◼◼FMYG◼◼◼F◼N◼TQG◼ : 78
mKate2.5 (SEQ ID NO:28)  : ◼◼TMR◼◼VV◼G◼◼LP◼◼F◼◼LA◼◼FMYG◼◼◼F◼N◼◼QG◼ : 78
mKate2.7C(SEQ ID NO:30)  : ◼◼TMR◼◼V◼◼G◼◼LP◼◼F◼◼LA◼◼FMYG◼◼◼F◼◼◼◼PG◼ : 78
DsRed2   (SEQ ID NO:37)  : HN◼VK◼◼VTKG◼◼LP◼◼◼W◼◼LSPQFQYG◼◼◼◼◼K◼◼AD◼ : 80
avGFP    (SEQ ID NO:36)  : KL◼LK◼ICTT◼G-KLP◼VP◼TLV◼◼FSYGVQC◼SRY◼DH◼K : 79
                             T64 k     GgpLPfa5diL   t  FYGs   5   h   6p

*         100        *         120
mKate2   (SEQ ID NO:2)   : --DF◼K◼◼◼PEGF◼◼ER◼◼◼Y◼D◼G◼◼L◼A◼◼◼◼◼◼◼◼◼ : 116
mKate2M1 (SEQ ID NO:4)   : --DF◼K◼◼◼PEGF◼◼ER◼◼◼Y◼D◼G◼◼L◼A◼◼◼◼◼◼◼◼◼ : 116
mKate2.5 (SEQ ID NO:28)  : --DF◼K◼◼◼PEGF◼◼ER◼◼◼Y◼D◼G◼◼L◼A◼◼◼◼◼◼◼◼◼ : 116
mKate2.7C(SEQ ID NO:30)  : --DF◼K◼◼◼PEGF◼◼ER◼◼◼Y◼D◼G◼◼L◼A◼◼◼◼◼◼◼◼◼ : 116
DsRed2   (SEQ ID NO:37)  : --DYKKL◼◼PEGFK◼ER◼MN◼D◼G◼◼A◼V◼◼◼◼◼◼◼QR◼F : 118
avGFP    (SEQ ID NO:36)  : QHDF◼KSAMPEGYVQERTIFF◼KDDGNYKTRAEVKF◼GDT◼ : 119
                             D5fK  sfPEG5 wERv    5eDgGv     t tqd sl2dgcl

*         140        *         160
mKate2   (SEQ ID NO:2)   : I◼◼V◼◼◼GVNF◼SNG◼VM◼KK◼L◼W◼◼◼T◼◼LY◼◼◼G◼E : 156
mKate2M1 (SEQ ID NO:4)   : I◼◼V◼◼◼GVNF◼SNG◼VM◼KK◼L◼W◼◼◼T◼◼LY◼◼◼G◼E : 156
mKate2.5 (SEQ ID NO:28)  : I◼◼V◼◼◼GVNF◼ANG◼VM◼KK◼L◼W◼◼◼T◼◼LY◼◼◼G◼E : 156
mKate2.7C(SEQ ID NO:30)  : I◼◼V◼◼◼GVNF◼ANG◼VM◼KK◼L◼W◼◼◼T◼◼MY◼◼◼G◼E : 156
DsRed2   (SEQ ID NO:37)  : I◼KV◼FIGVNF◼SDG◼VM◼KM◼MGW◼◼◼T◼RLY◼R◼◼V◼K : 158
avGFP    (SEQ ID NO:36)  : VNRIE◼◼GIDF◼KEDGNILGHK-LEYNYN◼SHNVYIMADKQK : 158
                           6y  6k   G61Fp 1Gp66qkKt6g5eas3e 6Yp dg   l

*         180        *         200
mKate2   (SEQ ID NO:2)   : ◼RA◼◼◼KL◼◼◼-◼L◼C◼◼K◼◼YR◼◼PAK--◼◼MP◼ : 193
mKate2M1 (SEQ ID NO:4)   : ◼ACD◼◼KL◼◼◼-◼L◼C◼◼◼◼◼YR◼◼PAK--◼◼MP◼ : 193
mKate2.5 (SEQ ID NO:28)  : ◼ACD◼◼KL◼◼◼-◼L◼C◼◼◼◼◼YR◼◼PAK--◼◼MP◼ : 193
mKate2.7C(SEQ ID NO:30)  : ◼ACD◼◼KL◼◼◼-◼L◼C◼◼◼◼◼YR◼◼PAT--◼◼MP◼ : 193
DsRed2   (SEQ ID NO:37)  : ETHK◼◼KLKD◼◼-◼Y◼VEFK◼IYMA◼◼◼PVQ-----LP◼Y : 192
avGFP    (SEQ ID NO:36)  : NGIK◼NF◼KIRHNIEDGSVQ◼ADHYQQNT◼IG◼GP◼LLP◼DN : 198
                           g    alK6     gg h    l  Y   kkP      6Pg

*         220     ]        240
mKate2   (SEQ ID NO:2)   : ◼Y◼◼R◼◼◼◼ERI◼-◼EADKE◼YV◼◼HEVAV◼◼◼YCDLPSKLGH◼ : 232
mKate2M1 (SEQ ID NO:4)   : ◼N◼◼R◼◼◼◼ERI◼-◼EADKE◼YV◼◼HEVAV◼◼◼YSTGGAGDGG◼ : 232
mKate2.5 (SEQ ID NO:28)  : ◼N◼◼R◼◼◼◼ERI◼-◼EADNE◼YV◼◼HEVAV◼◼◼YSTGGAGDGG◼ : 232
mKate2.7C(SEQ ID NO:30)  : ◼NV◼H◼◼◼◼ERI◼-◼EADDE◼YV◼◼HEVAV◼◼◼YSTGGAGDGG◼ : 232
DsRed2   (SEQ ID NO:37)  : YV◼AK◼◼DITS-HNEDY◼IV◼◼◼YERTEG◼HHLFL------  : 225
avGFP    (SEQ ID NO:36)  : HY◼STQSALS◼DPNEKRDHMVLLEFVT◼AGITHGMDELY◼   : 238
                           y 6d   l    k        t 6eq  E    ar
```

Fig. 1

```
                          SEQUENCE LISTING

<160> NUMBER OF SEQ ID NOS: 39

<210> SEQ ID NO 1
<211> LENGTH: 696
<212> TYPE: DNA
<213> ORGANISM: Artificial sequence
<220> FEATURE:
<223> OTHER INFORMATION: synthetic oligonucleotide for fluorescent
      protein mKate2

<400> SEQUENCE: 1
atggtgagcg agctgattaa ggagaacatg cacatgaagc tgtacatgga gggcaccgtg      60
aacaaccacc acttcaagtg cacatccgag ggcgaaggca agccctacga gggcacccag     120
accatgagaa tcaaggcggt cgagggcggc cctctcccct cgccttcga catcctggct      180 accagcttca tgtacggcag caaaaccttc atcaaccaca cccagggcat ccccgacttc     240
tttaagcagt ccttccccga gggcttcaca tgggagagag tcaccacata cgaagacggg     300
ggcgtgctga ccgctaccca ggacaccagc ctccaggacg gctgcctcat ctacaacgtc     360 aagatcgag gggtgaactt ccatccaac ggccctgtga tgcagaagaa aacactcggc       420
tgggaggcct ccaccgagac cctgtacccc gctgacggcg gcctggaagg cagagccgac     480
atggccctga agctcgtggg cggggccac ctgatctgca acttgaagac acatacaga       540 tccaagaaac ccgctaagaa cctcaagatg cccggcgtct actatgtgga cagaagactg     600
gaaagaatca aggaggccga caagagacc tacgtcgagc agcacgaggt ggctgtggcc      660
agatactgcg acctccctag caaactgggg cacaga                               696

<210> SEQ ID NO 2
<211> LENGTH: 232
<212> TYPE: PRT
<213> ORGANISM: Artificial sequence
<220> FEATURE:
<223> OTHER INFORMATION: synthetic polypeptide for fluorescent protein
      mKate2
<220> FEATURE:
<221> NAME/KEY: DOMAIN
<222> LOCATION: (4)..(222)
<223> OTHER INFORMATION: GFP-like domain

<400> SEQUENCE: 2

Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Ala Val Glu
        35                  40                  45

Gly Gly Pro Leu Pro Phe Ala Phe Asp Ile Leu Ala Thr Ser Phe Met
    50                  55                  60

Tyr Gly Ser Lys Thr Phe Ile Asn His Thr Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110
```

Asp Gly Cys Leu Ile Tyr Asn Val Lys Ile Arg Gly Val Asn Phe Pro
            115                 120                 125

Ser Asn Gly Pro Val Met Gln Lys Lys Thr Leu Gly Trp Glu Ala Ser
    130                 135                 140

Thr Glu Thr Leu Tyr Pro Ala Asp Gly Gly Leu Glu Gly Arg Ala Asp
145                 150                 155                 160

Met Ala Leu Lys Leu Val Gly Gly Gly His Leu Ile Cys Asn Leu Lys
                165                 170                 175

Thr Thr Tyr Arg Ser Lys Lys Pro Ala Lys Asn Leu Lys Met Pro Gly
            180                 185                 190

Val Tyr Tyr Val Asp Arg Arg Leu Glu Arg Ile Lys Glu Ala Asp Lys
        195                 200                 205

Glu Thr Tyr Val Glu Gln His Glu Val Ala Val Ala Arg Tyr Cys Asp
    210                 215                 220

Leu Pro Ser Lys Leu Gly His Arg
225                 230

<210> SEQ ID NO 3
<211> LENGTH: 699
<212> TYPE: DNA
<213> ORGANISM: Artificial sequence
<220> FEATURE:
<223> OTHER INFORMATION: synthetic oligonucleotide for fluorescent
      protein mKate2M1

<400> SEQUENCE: 3
atggtgagcg agctgattaa ggagaacatg cacatgaagc tgtacatgga gggcaccgtg    60
aacaaccacc acttcaagtg cacatccgag ggcgaaggca agccctacga gggcacccag   120
accatgagaa tcaaggcggt cgagggcggc cctctcccct cgccttcga catcctggct    180 accagcttca gtacggcag caaaaccttc atcaaccaca cccagggcat ccccgacttc    240
tttaagcagt ccttccccga gggcttcaca tgggagagag tcaccacata cgaagacggg    300
ggcgtgctga ccgctaccca ggacaccagc ctccaggacg gctgcctcat ctacaacgtc   360
aagatcagag gggtgaactt cccatccaac ggccctgtga tgcagaagaa aacactcggc   420
tgggaggcct ccaccgagac cctgtacccc gctgacggcg gcctggaagg cgcatgtgac   480
atggccctga gctcgtgggc ggggggccac ctgatctgca acttggagac acatacaga    540 tccaagaaac ccgctaagaa cctcaagatg cccggcgtct acaatgtgga cagaagactg   600
gaaagaatca aggaggccga caaagagacc tacgtcgagc agcacgaggt ggctgtggcc   660
agatactcta ctggtggcgc tggtgatgga ggtaaatga                          699

<210> SEQ ID NO 4
<211> LENGTH: 232
<212> TYPE: PRT
<213> ORGANISM: Artificial sequence
<220> FEATURE:
<223> OTHER INFORMATION: synthetic polypeptide for fluorescent protein
      mKate2M1
<220> FEATURE:
<221> NAME/KEY: DOMAIN
<222> LOCATION: (4)..(222)
<223> OTHER INFORMATION: GFP-like domain

<400> SEQUENCE: 4

Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Ala Val Glu
            35                  40                  45

Gly Gly Pro Leu Pro Phe Ala Phe Asp Ile Leu Ala Thr Ser Phe Met
 50                  55                  60

Tyr Gly Ser Lys Thr Phe Ile Asn His Thr Gln Gly Ile Pro Asp Phe
 65                  70                  75                  80

Phe Lys Gln Ser Phe Pro Glu Gly Phe Thr Trp Glu Arg Val Thr Thr
                 85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Pro
        115                 120                 125

Ser Asn Gly Pro Val Met Gln Lys Lys Thr Leu Gly Trp Glu Ala Ser
    130                 135                 140

Thr Glu Thr Leu Tyr Pro Ala Asp Gly Gly Leu Glu Gly Ala Cys Asp
145                 150                 155                 160

Met Ala Leu Lys Leu Val Gly Gly Gly His Leu Ile Cys Asn Leu Glu
                165                 170                 175

Thr Thr Tyr Arg Ser Lys Lys Pro Ala Lys Asn Leu Lys Met Pro Gly
            180                 185                 190

Val Tyr Asn Val Asp Arg Arg Leu Glu Arg Ile Lys Glu Ala Asp Lys
        195                 200                 205

Glu Thr Tyr Val Glu Gln His Glu Val Ala Val Ala Arg Tyr Ser Thr
    210                 215                 220

Gly Gly Ala Gly Asp Gly Gly Lys
225                 230

<210> SEQ ID NO 5
<211> LENGTH: 699
<212> TYPE: DNA
<213> ORGANISM: Artificial sequence
<220> FEATURE:
<223> OTHER INFORMATION: synthetic oligonucleotide for fluorescent
      protein pH-Redder-0.1

<400> SEQUENCE: 5
atggtgagcg agctgattaa ggagaacatg cacatgaagc tgtacatgga gggcaccgtg      60
aacaaccacc acttcaagtg cacatccgag ggcgaaggca agccctacga gggcacccag     120
accatgagaa tcaaggtggt cgagggcggc cctctcccct cgccttcga catcctggct      180 accagcttca tgtacggcag caaaaccttc atcaaccaca cccagggcat ccccgacttc     240
tttaagcagt ccttccctga gggcttcaca tgggagagag tcaccacata cgaagacggg     300
ggcgtgctga ccgctaccca ggacaccagc ctccaggacg gctgcctcat ctacaacgtc     360
aagatcagag gggtgaactt cccatccaac ggccctgtga tgcagaggaa aacactcggc     420
tgggaggcct ccaccgagat gctgtacccc gctgacggcg gcctggaagg cagaagcgac     480
atggccctga gctcgtgggg cggggggcac ctgatctgca acttggagac cacatacaga     540
tccaagaaac ccgctaagaa cctcaagatg cccggcgtct actatgtgga cagaagactg     600
gaaagaatca aggaggccga caaagagacc tacgtcgagc agcacgaggt ggctgtggcc     660
agatactgcg acctccctag caaattgggg cacagatga                            699

<210> SEQ ID NO 6
<211> LENGTH: 232
<212> TYPE: PRT
<213> ORGANISM: Artificial sequence

```
<220> FEATURE:
<223> OTHER INFORMATION: synthetic polypeptide for fluorescent protein
      pH-Redder-0.1
<220> FEATURE:
<221> NAME/KEY: DOMAIN
<222> LOCATION: (4)..(222)
<223> OTHER INFORMATION: GFP-like domain

<400> SEQUENCE: 6

Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Val Val Glu
        35                  40                  45

Gly Gly Pro Leu Pro Phe Ala Phe Asp Ile Leu Ala Thr Ser Phe Met
    50                  55                  60

Tyr Gly Ser Lys Thr Phe Ile Asn His Thr Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Pro
        115                 120                 125

Ser Asn Gly Pro Val Met Gln Arg Lys Thr Leu Gly Trp Glu Ala Ser
    130                 135                 140

Thr Glu Met Leu Tyr Pro Ala Asp Gly Gly Leu Glu Gly Arg Ser Asp
145                 150                 155                 160

Met Ala Leu Lys Leu Val Gly Gly Gly His Leu Ile Cys Asn Leu Glu
                165                 170                 175

Thr Thr Tyr Arg Ser Lys Lys Pro Ala Lys Asn Leu Lys Met Pro Gly
            180                 185                 190

Val Tyr Tyr Val Asp Arg Arg Leu Glu Arg Ile Lys Glu Ala Asp Lys
        195                 200                 205

Glu Thr Tyr Val Glu Gln His Glu Val Ala Val Ala Arg Tyr Cys Asp
    210                 215                 220

Leu Pro Ser Lys Leu Gly His Arg
225                 230

<210> SEQ ID NO 7
<211> LENGTH: 699
<212> TYPE: DNA
<213> ORGANISM: Artificial sequence
<220> FEATURE:
<223> OTHER INFORMATION: synthetic oligonucleotide for fluorescent
      protein mKate2M1pHsens1

<400> SEQUENCE: 7
atggtgagcg agctgattaa ggagaacatg cacatgaagc tgtacatgga gggcaccgtg      60
aacaaccacc acttcaagtg cacatccgag ggcgaaggca agccctacga gggcacccag     120
accatgagaa tcaaggcggt cgagggcggc cctctcccct cgccttcga  catcctggct     180 accagcttca tgtacggcag caaaaccttc atcaaccaca cccagggcat ccccgacttc     240
tttaagcagt ccttccccga gggcttcaca tgggagagag tcaccacata cgaagacggg     300
ggcgtgctga ccgctaccca ggacaccagc ctccaggacg gctgcctcat ctacaacgtc     360
aagatcagag gggtgaactt cccatccaac ggccctgtga tgcagaagaa aacactcggc     420
```

```
tgggaggcct ccaccgagac cctgtacccc gctgacggcg gcctggaagg cgcaggtgac    480
atggccctga agctcgtggg cggggggccac ctgatctgca acttggagac acatacaga    540 tccaagaaac ccgctaagaa cctcaagatg cccggcgtct acaatgtgga cagaagactg    600
gaaagaatca aggaggccga caaagagacc tacgtcgagc agcacgaggt ggctgtggcc    660
agatactcta ctggtggcgc tggtgatgga ggtaaatga                          699
```

<210> SEQ ID NO 8
<211> LENGTH: 232
<212> TYPE: PRT
<213> ORGANISM: Artificial sequence
<220> FEATURE:
<223> OTHER INFORMATION: synthetic polypeptide for fluorescent protein mKate2M1pHsens1
<220> FEATURE:
<221> NAME/KEY: DOMAIN
<222> LOCATION: (4)..(222)
<223> OTHER INFORMATION: GFP-like domain

<400> SEQUENCE: 8

```
Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Ala Val Glu
        35                  40                  45

Gly Gly Pro Leu Pro Phe Ala Phe Asp Ile Leu Ala Thr Ser Phe Met
    50                  55                  60

Tyr Gly Ser Lys Thr Phe Ile Asn His Thr Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Pro
        115                 120                 125

Ser Asn Gly Pro Val Met Gln Lys Lys Thr Leu Gly Trp Glu Ala Ser
    130                 135                 140

Thr Glu Thr Leu Tyr Pro Ala Asp Gly Gly Leu Glu Gly Ala Gly Asp
145                 150                 155                 160

Met Ala Leu Lys Leu Val Gly Gly Gly His Leu Ile Cys Asn Leu Glu
                165                 170                 175

Thr Thr Tyr Arg Ser Lys Lys Pro Ala Lys Asn Leu Lys Met Pro Gly
            180                 185                 190

Val Tyr Asn Val Asp Arg Arg Leu Glu Arg Ile Lys Glu Ala Asp Lys
        195                 200                 205

Glu Thr Tyr Val Glu Gln His Glu Val Ala Val Ala Arg Tyr Ser Thr
    210                 215                 220

Gly Gly Ala Gly Asp Gly Gly Lys
225                 230
```

<210> SEQ ID NO 9
<211> LENGTH: 699
<212> TYPE: DNA
<213> ORGANISM: Artificial sequence
<220> FEATURE:
<223> OTHER INFORMATION: synthetic oligonucleotide for fluorescent protein mKate2M1fold1

<400> SEQUENCE: 9

```
atggtgagcg agctgattaa ggagaacatg cacatgaagc tgtacatgga gggcaccgtg      60
aacaaccacc acttcaagtg cacatccgag ggcgaaggca agccctacga gggcacccag     120
accatgagaa tcaaggcggt cgagggcggc cctctcccct cgccttcga catcctggct      180 accagcttca tgtacggcag caaaaccttc atcaaccacc cccagggcat ccccgacttc     240
tttaagcagt ccttccccga gggcttcaca tgggagagag tcaccacata cgaagacggg     300
ggcgtgctga ccgctaccca ggacaccagc tccaggacg ctgcctcat ctacaacgtc      360 aagatcagag gggtgaactt ccatccaac ggccctgtga tgcagaagaa aacactcggc      420
tgggaggcct ccaccgagac cctgtacccc gctgacggcg cctggaagg cgcatgtgac      480 atggccctga agctcgtggg cgggggccac ctgatctgca acttggagac acatacaga      540 tccaagaaac ccgctaagaa cctcaagatg cccggcgtct acaatgtgga cagaagactg     600
gaaagaatca aggaggccga caacgagacc tacgtcgagc agcacgaggt ggctgtggcc     660
agatactcta ctggtggcgc tggtgatgga ggtaaatga                            699
```

<210> SEQ ID NO 10
<211> LENGTH: 232
<212> TYPE: PRT
<213> ORGANISM: Artificial sequence
<220> FEATURE:
<223> OTHER INFORMATION: synthetic polypeptide for fluorescent protein mKate2M1fold1
<220> FEATURE:
<221> NAME/KEY: DOMAIN
<222> LOCATION: (4)..(222)
<223> OTHER INFORMATION: GFP-like domain

<400> SEQUENCE: 10

```
Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Ala Val Glu
        35                  40                  45

Gly Gly Pro Leu Pro Phe Ala Phe Asp Ile Leu Ala Thr Ser Phe Met
    50                  55                  60

Tyr Gly Ser Lys Thr Phe Ile Asn His Pro Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Pro
        115                 120                 125

Ser Asn Gly Pro Val Met Gln Lys Lys Thr Leu Gly Trp Glu Ala Ser
    130                 135                 140

Thr Glu Thr Leu Tyr Pro Ala Asp Gly Gly Leu Glu Gly Ala Cys Asp
145                 150                 155                 160

Met Ala Leu Lys Leu Val Gly Gly Gly His Leu Ile Cys Asn Leu Glu
                165                 170                 175

Thr Thr Tyr Arg Ser Lys Lys Pro Ala Lys Asn Leu Lys Met Pro Gly
            180                 185                 190

Val Tyr Asn Val Asp Arg Arg Leu Glu Arg Ile Lys Glu Ala Asp Asn
        195                 200                 205

Glu Thr Tyr Val Glu Gln His Glu Val Ala Val Ala Arg Tyr Ser Thr
```

Gly Gly Ala Gly Asp Gly Gly Lys
225                 230

<210> SEQ ID NO 11
<211> LENGTH: 699
<212> TYPE: DNA
<213> ORGANISM: Artificial sequence
<220> FEATURE:
<223> OTHER INFORMATION: synthetic oligonucleotide for fluorescent
      protein mKate2M1fold2

<400> SEQUENCE: 11

```
atggtgagcg agctgattaa ggagaacatg cacatgaagc tgtacatgga gggcaccgtg      60
aacaaccacc acttcaagtg cacatccgag ggcgaaggca agccctacga gggcacccag     120
accatgagaa tcaaggcggt cgagggcggc cctctcccct cgccttcga catcctggct      180
accagcttca tgtacggcag caaaaccttc atcaaccacg gcagggcat ccccgacttc      240
tttaagcagt ccttccccga gggcttcaca tgggagagag tcaccacata cgaagacggg     300
ggcgtgctga ccgctaccca ggacaccagc ctccaggacg gctgcctcat ctacaacgtc     360
aagatcagag gggtgaactt cccatccaac ggccctgtga tgcagaagaa acactcggc     420
tgggaggcct ccaccgagac cctgtacccc gctgacggcg gcctggaagg cgcatgtgac     480
atggccctga agctcgtggg cggggccac ctgatctgca acttggagac acatacaga      540
tccaagaaac ccgctaagaa cctcaagatg cccggcgtct acaatgtgga cagaagactg     600
gaaagaatca aggaggccga ctctgagacc tacgtcgagc agcacgaggt ggctgtggcc     660
agatactcta ctggtggcgc tggtgatgga ggtaaatga                             699
```

<210> SEQ ID NO 12
<211> LENGTH: 232
<212> TYPE: PRT
<213> ORGANISM: Artificial sequence
<220> FEATURE:
<223> OTHER INFORMATION: synthetic polypeptide for fluorescent protein
      mKate2M1fold2
<220> FEATURE:
<221> NAME/KEY: DOMAIN
<222> LOCATION: (4)..(222)
<223> OTHER INFORMATION: GFP-like domain

<400> SEQUENCE: 12

Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Ala Val Glu
        35                  40                  45

Gly Gly Pro Leu Pro Phe Ala Phe Asp Ile Leu Ala Thr Ser Phe Met
    50                  55                  60

Tyr Gly Ser Lys Thr Phe Ile Asn His Gly Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Pro
        115                 120                 125

Ser Asn Gly Pro Val Met Gln Lys Lys Thr Leu Gly Trp Glu Ala Ser

```
                130               135               140
Thr Glu Thr Leu Tyr Pro Ala Asp Gly Gly Leu Glu Gly Ala Cys Asp
145                 150                 155                 160

Met Ala Leu Lys Leu Val Gly Gly His Leu Ile Cys Asn Leu Glu
                165                 170                 175

Thr Thr Tyr Arg Ser Lys Lys Pro Ala Lys Asn Leu Lys Met Pro Gly
            180                 185                 190

Val Tyr Asn Val Asp Arg Arg Leu Glu Arg Ile Lys Glu Ala Asp Ser
                195                 200                 205

Glu Thr Tyr Val Glu Gln His Glu Val Ala Val Ala Arg Tyr Ser Thr
            210                 215                 220

Gly Gly Ala Gly Asp Gly Gly Lys
225                 230
```

```
<210> SEQ ID NO 13
<211> LENGTH: 699
<212> TYPE: DNA
<213> ORGANISM: Artificial sequence
<220> FEATURE:
<223> OTHER INFORMATION: synthetic oligonucleotide for fluorescent
      protein mKate2M1stab1

<400> SEQUENCE: 13
atggtgagcg agctgattaa ggagaacatg cacatgaagc tgtacatgga gggcaccgtg      60
aacaaccacc acttcaagtg cacatccgag ggcgaaggca agccctacga gggcacccag     120
accatgagaa tcaaggcggt cgagggcggc cctctcccct tcgccttcga catcctggct     180
accagcttca tgtacggcag caaaaccttc atcaaccaca cccagggcat ccccgacttc     240
tttaagcagt cctccccga gggcttcaca tgggagagag tcaccacata cgaagacggg     300
ggcgtgctga ccgctaccca ggacaccagc tccaggacg ctgcctcat ctacaacgtc      360
aagatcagag gggtgaactt cccatccaac ggccctgtga tgcagaagaa aacactcggc     420
tgggaggcct ccaccgagac cctgtacccc gctgacggcg gcctggaagg cgcagttgac     480
atggccctga gctcgtgggg cgggggccac ctgatctgca acttggagac acatacagaa     540
tccaagaaac ccgctaagaa cctcaagatg cccggcgtct acaatgtgga cagaagactg     600
gaaagaatca aggaggccga caagagacc tacgtcgagc agcacgaggt ggctgtggcc      660
agatactcta ctggtggcgc tggtgatgga ggtaaatga                            699
```

```
<210> SEQ ID NO 14
<211> LENGTH: 232
<212> TYPE: PRT
<213> ORGANISM: Artificial sequence
<220> FEATURE:
<223> OTHER INFORMATION: synthetic polypeptide for fluorescent protein
      mKate2M1stab1
<220> FEATURE:
<221> NAME/KEY: DOMAIN
<222> LOCATION: (4)..(222)
<223> OTHER INFORMATION: GFP-like domain

<400> SEQUENCE: 14

Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
                20                  25                  30

Gly Lys Pro Tyr Glu Gly Thr Gln Thr Met Arg Ile Lys Ala Val Glu
            35                  40                  45

Gly Gly Pro Leu Pro Phe Ala Phe Asp Ile Leu Ala Thr Ser Phe Met
```

```
                50                  55                  60
Tyr Gly Ser Lys Thr Phe Ile Asn His Thr Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
                100                 105                 110

Asp Gly Cys Leu Ile Tyr Asn Val Lys Ile Arg Gly Val Asn Phe Pro
            115                 120                 125

Ser Asn Gly Pro Val Met Gln Lys Lys Thr Leu Gly Trp Glu Ala Ser
        130                 135                 140

Thr Glu Thr Leu Tyr Pro Ala Asp Gly Gly Leu Glu Gly Ala Val Asp
145                 150                 155                 160

Met Ala Leu Lys Leu Val Gly Gly Gly His Leu Ile Cys Asn Leu Glu
                165                 170                 175

Thr Thr Tyr Arg Ser Lys Lys Pro Ala Lys Asn Leu Lys Met Pro Gly
                180                 185                 190

Val Tyr Asn Val Asp Arg Arg Leu Glu Arg Ile Lys Glu Ala Asp Lys
            195                 200                 205

Glu Thr Tyr Val Glu Gln His Glu Val Ala Val Ala Arg Tyr Ser Thr
        210                 215                 220

Gly Gly Ala Gly Asp Gly Gly Lys
225                 230
```

<210> SEQ ID NO 15
<211> LENGTH: 699
<212> TYPE: DNA
<213> ORGANISM: Artificial sequence
<220> FEATURE:
<223> OTHER INFORMATION: synthetic oligonucleotide for fluorescent
      protein mKate2M1stab2

<400> SEQUENCE: 15

```
atggtgagcg agctgattaa ggagaacatg cacatgaagc tgtacatgga gggcaccgtg    60
aacaaccacc acttcaagtg cacatccgag ggcgaaggca agccctacga gggcacccag   120
accatgagaa tcaaggcggt cgagggcggc cctctcccct tcgccttcga catcctggct   180
accagcttca tgtacggcag caaaaccttc atcaaccaca cccagggcat ccccgacttc   240
tttaagcagt ccttccccga gggcttcaca tgggagagag tcaccacata cgaagacggg   300
ggcgtgctga ccgctaccca ggacaccagc tccaggacg ctgcctcat ctacaacgtc    360 aagatcagag gggtgaactt cccatccaac ggccctgtga tgcagaagaa acactcggc    420 tgggaggcct ccaccgagac cctgtacccc gctgacggcg gcctggaagg cgcaaatgac   480
atggccctga agctcgtggg cggggccac ctgatctgca acttggagac cacatacaga    540
tccaagaaac ccgctaagaa cctcaagatg cccggcgtct acaatgtgga cagaagactg   600
gaaagaatca aggaggccga caagagacc tacgtcgagc agcacgaggt ggctgtggcc   660
agatactcta ctggtggcgc tggtgatgga ggtaaatga                          699
```

<210> SEQ ID NO 16
<211> LENGTH: 232
<212> TYPE: PRT
<213> ORGANISM: Artificial sequence
<220> FEATURE:
<223> OTHER INFORMATION: synthetic polypeptide for fluorescent protein
      mKate2M1stab2
<220> FEATURE:
<221> NAME/KEY: DOMAIN
<222> LOCATION: (4)..(222)
<223> OTHER INFORMATION: GFP-like domain

<400> SEQUENCE: 16

| | | | | | | | | | | | | | | |
|---|---|---|---|---|---|---|---|---|---|---|---|---|---|---|
| Met | Val | Ser | Glu | Leu | Ile | Lys | Glu | Asn | Met | His | Met | Lys | Leu | Tyr | Met |
| 1 | | | | 5 | | | | | 10 | | | | | 15 | |

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Ala Val Glu
        35                  40                  45

Gly Gly Pro Leu Pro Phe Ala Phe Asp Ile Leu Ala Thr Ser Phe Met
    50                  55                  60

Tyr Gly Ser Lys Thr Phe Ile Asn His Thr Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Pro
        115                 120                 125

Ser Asn Gly Pro Val Met Gln Lys Lys Thr Leu Gly Trp Glu Ala Ser
    130                 135                 140

Thr Glu Thr Leu Tyr Pro Ala Asp Gly Gly Leu Glu Gly Ala Asn Asp
145                 150                 155                 160

Met Ala Leu Lys Leu Val Gly Gly Gly His Leu Ile Cys Asn Leu Glu
                165                 170                 175

Thr Thr Tyr Arg Ser Lys Lys Pro Ala Lys Asn Leu Lys Met Pro Gly
            180                 185                 190

Val Tyr Asn Val Asp Arg Arg Leu Glu Arg Ile Lys Glu Ala Asp Lys
        195                 200                 205

Glu Thr Tyr Val Glu Gln His Glu Val Ala Val Ala Arg Tyr Ser Thr
    210                 215                 220

Gly Gly Ala Gly Asp Gly Gly Lys
225                 230

<210> SEQ ID NO 17
<211> LENGTH: 699
<212> TYPE: DNA
<213> ORGANISM: Artificial sequence
<220> FEATURE:
<223> OTHER INFORMATION: synthetic oligonucleotide for fluorescent
      protein mKate2M1farred1

<400> SEQUENCE: 17
atggtgagcg agctgattaa ggagaacatg cacatgaagc tgtacatgga gggcaccgtg     60
aacaaccacc acttcaagtg cacatccgag ggcgaaggca agccctacga gggcacccag    120
accctgagaa tcaaggcggt cgagggcggc cctctcccct cgccttcga catcctggct     180 accagcttca tgtacggcag caaaaccttc atcaaccaca cccagggcat ccccgacttc    240
tttaagcagt ccttccccga gggcttcaca tgggagagag tcaccacata cgaagacggg    300
ggcgtgctga ccgctaccca ggacaccagc ctccaggacg gctgcctcat ctacaacgtc    360
aagatcagag gggtgaactt cccatccaac ggccctgtga tgcagaagaa aacactcggc    420
tgggaggcct ccaccgagac cctgtacccc gctgacggcg gcctggaagg cgcatgtgac    480
atggccctga agctcgtggg cggggccac ctgatctgca acttggagac cacatacaga    540
tccaagaaac ccgctaagaa cctcaagatg cccggcgtct acaatgtgga cagaagactg    600

```
gaaagaatca aggaggccga caaagagacc tacgtcgagc agcacgaggt ggctgtggcc      660
agatactcta ctggtggcgc tggtgatgga ggtaaatga                            699
```

<210> SEQ ID NO 18
<211> LENGTH: 232
<212> TYPE: PRT
<213> ORGANISM: Artificial sequence
<220> FEATURE:
<223> OTHER INFORMATION: synthetic polypeptide for fluorescent protein mKate2M1farred1
<220> FEATURE:
<221> NAME/KEY: DOMAIN
<222> LOCATION: (4)..(222)
<223> OTHER INFORMATION: GFP-like domain

<400> SEQUENCE: 18

```
Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Leu Arg Ile Lys Ala Val Glu
        35                  40                  45

Gly Gly Pro Leu Pro Phe Ala Phe Asp Ile Leu Ala Thr Ser Phe Met
    50                  55                  60

Tyr Gly Ser Lys Thr Phe Ile Asn His Thr Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Pro
        115                 120                 125

Ser Asn Gly Pro Val Met Gln Lys Lys Thr Leu Gly Trp Glu Ala Ser
    130                 135                 140

Thr Glu Thr Leu Tyr Pro Ala Asp Gly Gly Leu Glu Gly Ala Cys Asp
145                 150                 155                 160

Met Ala Leu Lys Leu Val Gly Gly Gly His Leu Ile Cys Asn Leu Glu
                165                 170                 175

Thr Thr Tyr Arg Ser Lys Lys Pro Ala Lys Asn Leu Lys Met Pro Gly
            180                 185                 190

Val Tyr Asn Val Asp Arg Arg Leu Glu Arg Ile Lys Glu Ala Asp Lys
        195                 200                 205

Glu Thr Tyr Val Glu Gln His Glu Val Ala Val Ala Arg Tyr Ser Thr
    210                 215                 220

Gly Gly Ala Gly Asp Gly Gly Lys
225                 230
```

<210> SEQ ID NO 19
<211> LENGTH: 699
<212> TYPE: DNA
<213> ORGANISM: Artificial sequence
<220> FEATURE:
<223> OTHER INFORMATION: synthetic oligonucleotide for fluorescent protein mKate2M1farred2

<400> SEQUENCE: 19

```
atggtgagcg agctgattaa ggagaacatg cacatgaagc tgtacatgga gggcaccgtg      60
aacaaccacc acttcaagtg cacatccgag ggcgaaggca gccctacga gggcacccag      120
```

```
accgtgagaa tcaaggcggt cgagggcggc cctctcccct tcgccttcga catcctggct    180
accagcttca tgtacggcag caaaaccttc atcaaccaca cccagggcat ccccgacttc    240
tttaagcagt ccttccccga gggcttcaca tgggagagag tcaccacata cgaagacggg    300
ggcgtgctga ccgctaccca ggacaccagc ctccaggacg gctgcctcat ctacaacgtc    360
aagatcagag gggtgaactt cccatccaac ggccctgtga tgcagaagaa aacactcggc    420
tgggaggcct ccaccgagac cctgtacccc gctgacggcg gcctggaagg cgcatgtgac    480
atggccctga agctcgtggg cggggggccac ctgatctgca acttggagac acatacaga    540 tccaagaaac ccgctaagaa cctcaagatg cccggcgtct acaatgtgga cagaagactg    600
gaaagaatca aggaggccga caaagagacc tacgtcgagc agcacgaggt ggctgtggcc    660
agatactcta ctggtggcgc tggtgatgga ggtaaatga                          699
```

<210> SEQ ID NO 20
<211> LENGTH: 232
<212> TYPE: PRT
<213> ORGANISM: Artificial sequence
<220> FEATURE:
<223> OTHER INFORMATION: synthetic polypeptide for fluorescent protein
      mKate2M1farred2
<220> FEATURE:
<221> NAME/KEY: DOMAIN
<222> LOCATION: (4)..(222)
<223> OTHER INFORMATION: GFP-like domain

<400> SEQUENCE: 20

Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
                20                  25                  30

Gly Lys Pro Tyr Glu Gly Thr Gln Thr Val Arg Ile Lys Ala Val Glu
            35                  40                  45

Gly Gly Pro Leu Pro Phe Ala Phe Asp Ile Leu Ala Thr Ser Phe Met
        50                  55                  60

Tyr Gly Ser Lys Thr Phe Ile Asn His Thr Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Pro
        115                 120                 125

Ser Asn Gly Pro Val Met Gln Lys Lys Thr Leu Gly Trp Glu Ala Ser
    130                 135                 140

Thr Glu Thr Leu Tyr Pro Ala Asp Gly Gly Leu Glu Gly Ala Cys Asp
145                 150                 155                 160

Met Ala Leu Lys Leu Val Gly Gly Gly His Leu Ile Cys Asn Leu Glu
                165                 170                 175

Thr Thr Tyr Arg Ser Lys Lys Pro Ala Lys Asn Leu Lys Met Pro Gly
            180                 185                 190

Val Tyr Asn Val Asp Arg Arg Leu Glu Arg Ile Lys Glu Ala Asp Lys
        195                 200                 205

Glu Thr Tyr Val Glu Gln His Glu Val Ala Val Ala Arg Tyr Ser Thr
    210                 215                 220

Gly Gly Ala Gly Asp Gly Gly Lys
225                 230

<210> SEQ ID NO 21
<211> LENGTH: 699
<212> TYPE: DNA
<213> ORGANISM: Artificial sequence
<220> FEATURE:
<223> OTHER INFORMATION: synthetic oligonucleotide for fluorescent
     protein mKate2M1farred3

<400> SEQUENCE: 21

```
atggtgagcg agctgattaa ggagaacatg cacatgaagc tgtacatgga gggcaccgtg      60
aacaaccacc acttcaagtg cacatccgag ggcgaaggca agccctacga gggcacccag     120
accgtgagaa tcaaggcggt cgagggcggc cctctcccct cgccttcga catcctggct      180
accagcttca tgtacggcag caaaaccttc atcaaccaca cccagggcat ccccgacttc     240
tttaagcagt ccttccccga gggcttcaca tgggagagag tcaccacata cgaagacggg     300
ggcgtgctga ccgctaccaa cgacaccagc ctccaggacg gctgcctcat ctacaacgtc     360
aagatcagag gggtgaactt cccatccaac ggccctgtga tgcagaagaa aacactcggc     420
tgggaggcct ccaccgagac cctgtacccc gctgacggcg gcctggaagg cgcatgtgac     480
atggccctga gctcgtgggg cggggggccac ctgatctgca acttggagac acatacaga    540
tccaagaaac ccgctaagaa cctcaagatg cccggcgtct acaatgtgga cagaagactg     600
gaaagaatca ggaggccga caaagagacc tacgtcgagc agcacgaggt ggctgtggcc      660
agatactcta ctggtggcgc tggtgatgga ggtaaatga                            699
```

<210> SEQ ID NO 22
<211> LENGTH: 232
<212> TYPE: PRT
<213> ORGANISM: Artificial sequence
<220> FEATURE:
<223> OTHER INFORMATION: synthetic polypeptide for fluorescent protein
     mKate2M1farred3
<220> FEATURE:
<221> NAME/KEY: DOMAIN
<222> LOCATION: (4)..(222)
<223> OTHER INFORMATION: GFP-like domain

<400> SEQUENCE: 22

```
Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Val Arg Ile Lys Ala Val Glu
        35                  40                  45

Gly Gly Pro Leu Pro Phe Ala Phe Asp Ile Leu Ala Thr Ser Phe Met
    50                  55                  60

Tyr Gly Ser Lys Thr Phe Ile Asn His Thr Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Asn Asp Thr Ser Leu Gln
            100                 105                 110

Asp Gly Cys Leu Ile Tyr Asn Val Lys Ile Arg Gly Val Asn Phe Pro
        115                 120                 125

Ser Asn Gly Pro Val Met Gln Lys Lys Thr Leu Gly Trp Glu Ala Ser
    130                 135                 140

Thr Glu Thr Leu Tyr Pro Ala Asp Gly Gly Leu Glu Gly Ala Cys Asp
145                 150                 155                 160
```

```
Met Ala Leu Lys Leu Val Gly Gly Gly His Leu Ile Cys Asn Leu Glu
            165                 170                 175
Thr Thr Tyr Arg Ser Lys Lys Pro Ala Lys Asn Leu Lys Met Pro Gly
            180                 185                 190
Val Tyr Asn Val Asp Arg Arg Leu Glu Arg Ile Lys Glu Ala Asp Lys
        195                 200                 205
Glu Thr Tyr Val Glu Gln His Glu Val Ala Val Ala Arg Tyr Ser Thr
    210                 215                 220
Gly Gly Ala Gly Asp Gly Gly Lys
225                 230

<210> SEQ ID NO 23
<211> LENGTH: 699
<212> TYPE: DNA
<213> ORGANISM: Artificial sequence
<220> FEATURE:
<223> OTHER INFORMATION: synthetic oligonucleotide for fluorescent
      protein mKate2M1orange1

<400> SEQUENCE: 23
atggtgagcg agctgattaa ggagaacatg cacatgaagc tgtacatgga gggcaccgtg      60
aacaaccacc acttcaagtg cacatccgag ggcgaaggca agccctacga gggcacccag     120
accatgagaa tcaaggcggt cgagggcggc cctctcccct cgccttcga catcctggct      180
accagcttca tgtacggcag caaaaccttc atcaaccaca cccagggcat ccccgacttc     240
tttaagcagt ccttccccga gggcttcaca tgggagagag tcaccacata cgaagacggg     300
ggcgtgctga ccgctaccca ggacaccagc ctccaggacg gctgcctcat ctacaacgtc     360
aagatcagag gggtgaactt cccatccaac ggccctgtga tgcagaagaa aacactcggc     420
tgggaggcct gtaccgagac cctgtacccc gctgacggcg gcctgaaggg cgcagttgac     480
atggccctga gctcgtgggc gggggccac ctgatctgca acttggagac acatacagaa     540
tccaagaaac ccgctaagaa cctcaagatg cccggcgtct acaatgtgga ctacagactg     600
gaaagaatca aggaggccga caaagagacc tacgtcgagc agcacgaggt ggctgtggcc     660
agatactcta ctggtggcgc tggtgatgga ggtaaatga                             699

<210> SEQ ID NO 24
<211> LENGTH: 232
<212> TYPE: PRT
<213> ORGANISM: Artificial sequence
<220> FEATURE:
<223> OTHER INFORMATION: synthetic polypeptide for fluorescent protein
      mKate2M1orange1
<220> FEATURE:
<221> NAME/KEY: DOMAIN
<222> LOCATION: (4)..(222)
<223> OTHER INFORMATION: GFP-like domain

<400> SEQUENCE: 24

Met Val Ser Glu Leu Ile Lys Glu Asn Met His Met Lys Leu Tyr Met
1               5                   10                  15
Glu Gly Thr Val Asn Asn His His Phe Lys Cys Thr Ser Glu Gly Glu
            20                  25                  30
Gly Lys Pro Tyr Glu Gly Thr Gln Thr Met Arg Ile Lys Ala Val Glu
        35                  40                  45
Gly Gly Pro Leu Pro Phe Ala Phe Asp Ile Leu Ala Thr Ser Phe Met
    50                  55                  60
Tyr Gly Ser Lys Thr Phe Ile Asn His Thr Gln Gly Ile Pro Asp Phe
65                  70                  75                  80
```

```
Phe Lys Gln Ser Phe Pro Glu Gly Phe Thr Trp Glu Arg Val Thr Thr
                85                  90                  95
Tyr Glu Asp Gly Gly Val Leu Thr Ala Thr Gln Asp Thr Ser Leu Gln
            100                 105                 110
Asp Gly Cys Leu Ile Tyr Asn Val Lys Ile Arg Gly Val Asn Phe Pro
        115                 120                 125
Ser Asn Gly Pro Val Met Gln Lys Lys Thr Leu Gly Trp Glu Ala Cys
130                 135                 140
Thr Glu Thr Leu Tyr Pro Ala Asp Gly Gly Leu Glu Gly Ala Thr Asp
145                 150                 155                 160
Met Ala Leu Lys Leu Val Gly Gly Gly His Leu Ile Cys Asn Leu Glu
                165                 170                 175
Thr Thr Tyr Arg Ser Lys Lys Pro Ala Lys Asn Leu Lys Met Pro Gly
            180                 185                 190
Val Tyr Asn Val Asp Tyr Arg Leu Glu Arg Ile Lys Glu Ala Asp Lys
        195                 200                 205
Glu Thr Tyr Val Glu Gln His Glu Val Ala Val Ala Arg Tyr Ser Thr
210                 215                 220
Gly Gly Ala Gly Asp Gly Gly Lys
225                 230
```

<210> SEQ ID NO 25
<211> LENGTH: 699
<212> TYPE: DNA
<213> ORGANISM: Artificial sequence
<220> FEATURE:
<223> OTHER INFORMATION: synthetic oligonucleotide for fluorescent protein mKate2M1photo1

<400> SEQUENCE: 25

```
atggtgagcg agctgattaa ggagaacatg cacatgaagc tgtacatgga gggcaccgtg    60
aacaaccacc acttcaagtg cacatccgag ggcgaaggca agccctacga gggcacccag   120
accatgagaa tcaaggcggt cgagggcggc cctctcccct tcgccttcga catcctggct   180
accagcttca tgtacggcag caaaaccttc atcaaccaca cccagggcat ccccgacttc   240
tttaagcagt ccttccccga gggcttcaca tgggagagag tcaccacata cgaagacggg   300
ggcgtgctga ccgctaccca ggacaccagc ctccaggacg gctgcctcat ctacaacgtc   360
aagatcagag gggtgaactt cccatccaac ggccctgtga tgcagaagaa acactcggc   420
tgggaggccc acaccgagac cctgtacccc gctgacggcg gcctggaagg cgcatgtgac   480
atggccctga gctcgtgggc gggggccac ctgatctgca acttggagac acatacaga   540
tccaagaaac ccgctaagaa cctcaagatg cccggcgtct acaatgtgga ccacagactg   600
gaaagaatca aggaggccga caaagagacc tacgtcgagc agcacgaggt ggctgtggcc   660
agatactcta ctggtggcgc tggtgatgga ggtaaatga                          699
```

<210> SEQ ID NO 26
<211> LENGTH: 232
<212> TYPE: PRT
<213> ORGANISM: Artificial sequence
<220> FEATURE:
<223> OTHER INFORMATION: synthetic polypeptide for fluorescent protein mKate2M1photo1
<220> FEATURE:
<221> NAME/KEY: DOMAIN
<222> LOCATION: (4)..(222)
<223> OTHER INFORMATION: GFP-like domain

<400> SEQUENCE: 26

```
Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Ala Val Glu
        35                  40                  45

Gly Gly Pro Leu Pro Phe Ala Phe Asp Ile Leu Ala Thr Ser Phe Met
    50                  55                  60

Tyr Gly Ser Lys Thr Phe Ile Asn His Thr Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Pro
        115                 120                 125

Ser Asn Gly Pro Val Met Gln Lys Lys Thr Leu Gly Trp Glu Ala His
    130                 135                 140

Thr Glu Thr Leu Tyr Pro Ala Asp Gly Gly Leu Glu Gly Ala Cys Asp
145                 150                 155                 160

Met Ala Leu Lys Leu Val Gly Gly Gly His Leu Ile Cys Asn Leu Glu
                165                 170                 175

Thr Thr Tyr Arg Ser Lys Lys Pro Ala Lys Asn Leu Lys Met Pro Gly
            180                 185                 190

Val Tyr Asn Val Asp His Arg Leu Glu Arg Ile Lys Glu Ala Asp Lys
        195                 200                 205

Glu Thr Tyr Val Glu Gln His Glu Val Ala Val Ala Arg Tyr Ser Thr
    210                 215                 220

Gly Gly Ala Gly Asp Gly Gly Lys
225                 230

<210> SEQ ID NO 27
<211> LENGTH: 696
<212> TYPE: DNA
<213> ORGANISM: Artificial sequence
<220> FEATURE:
<223> OTHER INFORMATION: synthetic oligonucleotide for fluorescent
      protein mKate2.5

<400> SEQUENCE: 27
atggtgagcg agctgattaa ggagaacatg cacatgaagc tgtacatgga gggcaccgtg      60
aacaaccacc acttcaagtg cacatccgag ggcgaaggca agccctacga gggcacccag     120
accatgagaa tcaaggtcgt cgagggcggc cctctcccct cgccttcga catcctggct     180 accagcttca tgtacggcag caaaaccttc atcaaccacc ctcagggcat ccccgacttc     240
tttaagcagt cctteccctga gggcttcaca tggagagag tcaccacata cgaagacggg     300
ggcgtgctga ccgctaccca ggacaccagc ctccaggacg gctgcctcat ctacaacgtc     360
aagattagag gggtgaactt cccagccaac ggccctgtga tgcagaagaa aacactcggc     420
tgggaggcct ccaccgagac gctgtacccc gctgacggcg gcctggaagg cgcatgtgac     480
atggccctga gctcgtgggt cggggggccac ctgatctgca acttggagac cacatacaga     540
tccaagaaac ccgctaagaa cctcaagatg cccggcgtct acaacgtgga caggagactg     600
gaaagaatca aggaggccga caatgagacc tacgtcgagc agcacgaggt ggctgtggcc     660
agatactcta ctggtggcgc tggtgatgga ggtaaa                              696
```

-continued

<210> SEQ ID NO 28
<211> LENGTH: 232
<212> TYPE: PRT
<213> ORGANISM: Artificial sequence
<220> FEATURE:
<223> OTHER INFORMATION: synthetic polypeptide for fluorescent protein
      mKate2.5
<220> FEATURE:
<221> NAME/KEY: DOMAIN
<222> LOCATION: (4)..(222)
<223> OTHER INFORMATION: GFP-like domain

<400> SEQUENCE: 28

```
Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Val Val Glu
        35                  40                  45

Gly Gly Pro Leu Pro Phe Ala Phe Asp Ile Leu Ala Thr Ser Phe Met
    50                  55                  60

Tyr Gly Ser Lys Thr Phe Ile Asn His Pro Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Pro
        115                 120                 125

Ala Asn Gly Pro Val Met Gln Lys Lys Thr Leu Gly Trp Glu Ala Ser
    130                 135                 140

Thr Glu Thr Leu Tyr Pro Ala Asp Gly Gly Leu Glu Gly Ala Cys Asp
145                 150                 155                 160

Met Ala Leu Lys Leu Val Gly Gly His Leu Ile Cys Asn Leu Glu
                165                 170                 175

Thr Thr Tyr Arg Ser Lys Lys Pro Ala Lys Asn Leu Lys Met Pro Gly
            180                 185                 190

Val Tyr Asn Val Asp Arg Arg Leu Glu Arg Ile Lys Glu Ala Asp Asn
        195                 200                 205

Glu Thr Tyr Val Glu Gln His Glu Val Ala Val Ala Arg Tyr Ser Thr
    210                 215                 220

Gly Gly Ala Gly Asp Gly Gly Lys
225                 230
```

<210> SEQ ID NO 29
<211> LENGTH: 696
<212> TYPE: DNA
<213> ORGANISM: Artificial sequence
<220> FEATURE:
<223> OTHER INFORMATION: synthetic oligonucleotide for fluorescent
      protein mKate2.7C

<400> SEQUENCE: 29
atggtgagcg agctgattaa ggagaacatg cccatgaagc tgtacatgga gggcaccgtg      60
aacaaccacc acttcaagtg cacatccgag ggcgaaggca agccctacga gggcacccag     120
accatgagaa tcaaggtcgt cgagggcggc cctctcccct tcgccttcga catcctggct     180
accagcttca tgtacggcag cagaaccttc atcaagcacc ctcggggcat ccccgacttc     240
tttaagcagt ccttccctga gggcttcaca tgggagagag tcaccacata cgaagacggg     300
```

-continued

```
ggcgtgctga ccgctaccca ggacaccagc ctccaggacg gctgcctcat ctacaacgtc    360
aaggttagag gggtgaactt cccagccaac ggccctgtga tgcagaagaa aacactcggc    420
tgggaggcct ccaccgagac gatgtacccc gctgacggcg gcctggaagg cgcatgtgac    480
atggccctga agctcgtggg cgggggccac ctgatctgca accttgagac cacatacaga    540
tccaagaaac ccgctacgaa cctcaagatg cccggcgtct acaacgtgga ccacagactg    600
gaaagaatca aggaggccga cgatgagacc tacgtcgagc agcacgaggt ggctgtggcc    660
agatactcta ctggtggcgc tggtgatgga ggtaaa                              696
```

```
<210> SEQ ID NO 30
<211> LENGTH: 232
<212> TYPE: PRT
<213> ORGANISM: Artificial sequence
<220> FEATURE:
<223> OTHER INFORMATION: synthetic polypeptide for fluorescent protein
      mKate2.7C
<220> FEATURE:
<221> NAME/KEY: DOMAIN
<222> LOCATION: (4)..(222)
<223> OTHER INFORMATION: GFP-like domain

<400> SEQUENCE: 30
```

Met Val Ser Glu Leu Ile Lys Glu Asn Met Pro Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Val Val Glu
        35                  40                  45

Gly Gly Pro Leu Pro Phe Ala Phe Asp Ile Leu Ala Thr Ser Phe Met
    50                  55                  60

Tyr Gly Ser Arg Thr Phe Ile Lys His Pro Pro Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Val Arg Gly Val Asn Phe Pro
        115                 120                 125

Ala Asn Gly Pro Val Met Gln Lys Lys Thr Leu Gly Trp Glu Ala Ser
    130                 135                 140

Thr Glu Thr Met Tyr Pro Ala Asp Gly Gly Leu Glu Gly Ala Cys Asp
145                 150                 155                 160

Met Ala Leu Lys Leu Val Gly Gly Gly His Leu Ile Cys Asn Leu Glu
                165                 170                 175

Thr Thr Tyr Arg Ser Lys Lys Pro Ala Thr Asn Leu Lys Met Pro Gly
            180                 185                 190

Val Tyr Asn Val Asp His Arg Leu Glu Arg Ile Lys Glu Ala Asp Asp
        195                 200                 205

Glu Thr Tyr Val Glu Gln His Glu Val Ala Val Ala Arg Tyr Ser Thr
    210                 215                 220

Gly Gly Ala Gly Asp Gly Gly Lys
225                 230

```
<210> SEQ ID NO 31
<211> LENGTH: 10
<212> TYPE: PRT
<213> ORGANISM: Artificial sequence
```

<220> FEATURE:
<223> OTHER INFORMATION: synthetic peptide of the substitute C-terminal tail

<400> SEQUENCE: 31

Ser Thr Gly Gly Ala Gly Asp Gly Gly Lys
1               5                   10

<210> SEQ ID NO 32
<211> LENGTH: 696
<212> TYPE: DNA
<213> ORGANISM: Artificial sequence
<220> FEATURE:
<223> OTHER INFORMATION: synthetic oligonucleotide for fluorescent protein mKate2.7C-PA1

<400> SEQUENCE: 32

```
atggtgagcg agctgattaa ggagaacatg cccatgaagc tgtacatgga gggcaccgtg     60
aacaaccacc acttcaagtg cacatccgag ggcgaaggca agccctacga gggcacccag    120
accatgagaa tcaaggtcgt cgagggcggc cctctcccct tcgccttcga catcctggct    180
accagcttca gtacggcag cagaaccttc atcaagcacc ctccgggcat ccccgacttc    240
tttaagcagt ccttccctga gggcttcaca tgggagagag tcaccacata cgaagacggg    300
ggcgtgctga ccgctaccca ggacaccagc ctccaggacg ctgcctcat ctacaacgtc     360
aaggttagag gggtgaactt cccagccaac ggccctgtga tgcagaagaa aacactcggc    420
tgggaggccg ccaccgagac gatgtacccc gctgacggcg gcctggaagg cgcagctgac    480
atggccctga agctcgtggg cggggggccac ctgatctgca accttgagac acatacaga    540
tccaagaaac ccgctacgaa cctcaagatg cccggcgtct acaacgtgga ccacagactg    600
gaaagaatca aggaggccga cgatgagacc tacgtcgagc agcacgaggt ggctgtggcc    660
agatactcta ctggtggcgc tggtgatgga ggtaaa                               696
```

<210> SEQ ID NO 33
<211> LENGTH: 232
<212> TYPE: PRT
<213> ORGANISM: Artificial sequence
<220> FEATURE:
<223> OTHER INFORMATION: synthetic polypeptide for fluorescent protein mKate2.7C-PA1
<220> FEATURE:
<221> NAME/KEY: DOMAIN
<222> LOCATION: (4)..(222)
<223> OTHER INFORMATION: GFP-like domain

<400> SEQUENCE: 33

Met Val Ser Glu Leu Ile Lys Glu Asn Met Pro Met Lys Leu Tyr Met
1               5                   10                  15

Glu Gly Thr Val Asn Asn His His Phe Lys Cys Thr Ser Glu Gly Glu
                20                  25                  30

Gly Lys Pro Tyr Glu Gly Thr Gln Thr Met Arg Ile Lys Val Val Glu
            35                  40                  45

Gly Gly Pro Leu Pro Phe Ala Phe Asp Ile Leu Ala Thr Ser Phe Met
        50                  55                  60

Tyr Gly Ser Arg Thr Phe Ile Lys His Pro Pro Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

```
Asp Gly Cys Leu Ile Tyr Asn Val Lys Val Arg Gly Val Asn Phe Pro
            115                 120                 125
Ala Asn Gly Pro Val Met Gln Lys Lys Thr Leu Gly Trp Glu Ala Ala
        130                 135                 140
Thr Glu Thr Met Tyr Pro Ala Asp Gly Gly Leu Glu Gly Ala Ala Asp
145                 150                 155                 160
Met Ala Leu Lys Leu Val Gly Gly Gly His Leu Ile Cys Asn Leu Glu
                165                 170                 175
Thr Thr Tyr Arg Ser Lys Lys Pro Ala Thr Asn Leu Lys Met Pro Gly
            180                 185                 190
Val Tyr Asn Val Asp His Arg Leu Glu Arg Ile Lys Glu Ala Asp Asp
        195                 200                 205
Glu Thr Tyr Val Glu Gln His Glu Val Ala Val Ala Arg Tyr Ser Thr
210                 215                 220
Gly Gly Ala Gly Asp Gly Gly Lys
225                 230
```

<210> SEQ ID NO 34
<211> LENGTH: 696
<212> TYPE: DNA
<213> ORGANISM: Artificial sequence
<220> FEATURE:
<223> OTHER INFORMATION: synthetic oligonucleotide for fluorescent
      protein mKate2.7C-PA2

<400> SEQUENCE: 34

```
atggtgagcg agctgattaa ggagaacatg cccatgaagc tgtacatgga gggcaccgtg      60
aacaaccacc acttcaagtg cacatccgag ggcgaaggca agccctacga gggcacccag     120
accatgagaa tcaaggtcgt cgagggcggc cctctcccct cgccttcga catcctggct      180
accagcttca tgtacggcag caaaaccttc atcaagcacc ctccgggcat ccccgacttc     240
tttaagcagt ccttccctga gggcttcaca tgggagagag tcaccacata cgaagacggg     300
ggcgtgctga ccgctaccca ggacaccagc ctccaggacg gctgcctcat ctacaacgtc     360
aaggttagag gggtgaactt cccagccaac ggccctgtga tgcagaagaa aacactcggc     420
tgggaggccc acaccgagac gatgtacccc gctgacggcg gcctggaagg cgcatgtgac     480
atggccctga gctcgtgggc ggggggccac ctgatctgca accttgagac cacatacaga     540
tccaagaaac ccgctacgaa cctcaagatg cccggcgtct acaacgtgga ccacagactg     600
gaaagaatca aggaggccga cgatgagacc tacgtcgagc agcacgaggt ggctgtggcc     660
agatactcta ctggtggcgc tggtgatgga ggtaaa                              696
```

<210> SEQ ID NO 35
<211> LENGTH: 232
<212> TYPE: PRT
<213> ORGANISM: Artificial sequence
<220> FEATURE:
<223> OTHER INFORMATION: synthetic polypeptide for fluorescent protein
      mKate2.7C-PA2
<220> FEATURE:
<221> NAME/KEY: DOMAIN
<222> LOCATION: (4)..(222)
<223> OTHER INFORMATION: GFP-like domain

<400> SEQUENCE: 35

```
Met Val Ser Glu Leu Ile Lys Glu Asn Met Pro Met Lys Leu Tyr Met
1               5                   10                  15
Glu Gly Thr Val Asn Asn His His Phe Lys Cys Thr Ser Glu Gly Glu
            20                  25                  30
```

Gly Lys Pro Tyr Glu Gly Thr Gln Thr Met Arg Ile Lys Val Val Glu
                35                  40                  45

Gly Gly Pro Leu Pro Phe Ala Phe Asp Ile Leu Ala Thr Ser Phe Met
    50                  55                  60

Tyr Gly Ser Lys Thr Phe Ile Lys His Pro Pro Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
                100                 105                 110

Asp Gly Cys Leu Ile Tyr Asn Val Lys Val Arg Gly Val Asn Phe Pro
            115                 120                 125

Ala Asn Gly Pro Val Met Gln Lys Lys Thr Leu Gly Trp Glu Ala His
130                 135                 140

Thr Glu Thr Met Tyr Pro Ala Asp Gly Gly Leu Glu Gly Ala Cys Asp
145                 150                 155                 160

Met Ala Leu Lys Leu Val Gly Gly Gly His Leu Ile Cys Asn Leu Glu
                165                 170                 175

Thr Thr Tyr Arg Ser Lys Lys Pro Ala Thr Asn Leu Lys Met Pro Gly
                180                 185                 190

Val Tyr Asn Val Asp His Arg Leu Glu Arg Ile Lys Glu Ala Asp Asp
            195                 200                 205

Glu Thr Tyr Val Glu Gln His Glu Val Ala Val Ala Arg Tyr Ser Thr
210                 215                 220

Gly Gly Ala Gly Asp Gly Gly Lys
225                 230

<210> SEQ ID NO 36
<211> LENGTH: 238
<212> TYPE: PRT
<213> ORGANISM: Aequorea victoria
<220> FEATURE:
<221> NAME/KEY: DOMAIN
<222> LOCATION: (6)..(229)
<223> OTHER INFORMATION: GFP-like domain

<400> SEQUENCE: 36

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
            165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 37
<211> LENGTH: 225
<212> TYPE: PRT
<213> ORGANISM: Artificial sequence
<220> FEATURE:
<223> OTHER INFORMATION: synthetic polypeptide for fluorescent protein
      DsRed2

<400> SEQUENCE: 37

Met Ala Ser Ser Glu Asn Val Ile Thr Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Ala Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Thr His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ala Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 38
<211> LENGTH: 696
<212> TYPE: DNA
<213> ORGANISM: Artificial Sequence
<220> FEATURE:
<223> OTHER INFORMATION: synthetic oligonucleotide for fluorescent
      protein mKate2.6

<400> SEQUENCE: 38

```
atggtgagcg agctgattaa ggagaacatg cacatgaagc tgtacatgga gggcaccgtg      60
aacaaccacc acttcaagtg cacatccgag ggcgaaggca agccctacga gggcacccag     120
accatgagaa tcaaggtcgt cgagggcggc cctctcccct cgccttcga  catcctggct     180
accagcttca tgtacggcag cagaaccttc atcaaccacc ctcagggcat ccccgacttc     240
tttaagcagt ccttccctga gggcttcaca tgggagagag tcaccacata cgaagacggg     300
ggcgtgctga ccgctaccca ggacaccagc ctccaggacg gctgcctcat ctacaacgtc     360
aagattagag gggtgaactt cccagccaac ggccctgtga tgcagaagaa aacactcggc     420
tgggaggcct ccaccgagac gctgtacccc gctgacggcg gcctggaagg cgcatgtgac     480
atggccctga agctcgtggg cggggccac  ctgatctgca acttggagac acatacaga     540
tccaagaaac ccgctaagaa cctcaagatg cccggcgtct acaacgtgga ccacagactg     600
gaaagaatca ggaggccga  caatgagacc tacgtcgagc agcacgaggt ggctgtggcc     660
agatactcta ctggtggcgc tggtgatgga ggtaaa                              696
```

<210> SEQ ID NO 39
<211> LENGTH: 232
<212> TYPE: PRT
<213> ORGANISM: Artificial Sequence
<220> FEATURE:
<223> OTHER INFORMATION: synthetic polypeptide for fluorescent protein
      mKate2.6
<220> FEATURE:
<221> NAME/KEY: DOMAIN
<222> LOCATION: (4)..(222)
<223> OTHER INFORMATION: GFP-like domain

<400> SEQUENCE: 39

```
Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Val Val Glu
        35                  40                  45

Gly Gly Pro Leu Pro Phe Ala Phe Asp Ile Leu Ala Thr Ser Phe Met
    50                  55                  60

Tyr Gly Ser Arg Thr Phe Ile Asn His Pro Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Pro
        115                 120                 125

Ala Asn Gly Pro Val Met Gln Lys Lys Thr Leu Gly Trp Glu Ala Ser
    130                 135                 140

Thr Glu Thr Leu Tyr Pro Ala Asp Gly Gly Leu Glu Gly Ala Cys Asp
145                 150                 155                 160

Met Ala Leu Lys Leu Val Gly Gly Gly His Leu Ile Cys Asn Leu Glu
                165                 170                 175

Thr Thr Tyr Arg Ser Lys Lys Pro Ala Lys Asn Leu Lys Met Pro Gly
            180                 185                 190

Val Tyr Asn Val Asp His Arg Leu Glu Arg Ile Lys Glu Ala Asp Asn
        195                 200                 205
```

```
Glu Thr Tyr Val Glu Gln His Glu Val Ala Val Ala Arg Tyr Ser Thr
    210                 215                 220
Gly Gly Ala Gly Asp Gly Gly Lys
225                 230
```

MODIFIED FLUORESCENT PROTEINS AND METHODS FOR USING SAME

CROSS REFERENCE TO RELATED APPLICATIONS

Pursuant to 35 U.S.C. §119 (e), this application claims priority to the filing date of the U.S. Provisional Patent Application Ser. No. 61/215,912 filed May 11, 2009; the disclosure of which are herein incorporated by reference.

FIELD OF THE INVENTION

Fluorescent proteins and nucleic acids that encode fluorescent proteins are provided. Also provided are methods for their use, and reagents, devices and kits for use in these methods.

BACKGROUND

Labeling of a protein, cell, or organism of interest plays a prominent role in many biochemical, molecular biological, and medical diagnostic applications. A variety of different labels have been developed and used in the art, including radiolabels, chromolabels, fluorescent labels, chemiluminescent labels, and the like, with varying properties and optimal uses. However, there is continued interest in the development of new labels. Of particular interest is the development of new protein labels, including fluorescent protein labels.

Green Fluorescent Protein (GFP) from the hydromedusa *Aequorea aequorea/Aequorea victoria* (*A. victoria*) was identified by Johnson et al., J. Cell Comp. Physiol. (1962) 60:85-104 as a secondary emitter of the jellyfish's bioluminescent system, transforming blue light from the photoprotein aequorin into green light. The cDNA encoding *A. victoria* GFP (avGFP) was cloned as reported in Prasher et al., Gene (1992) 111:229-33 (SEQ ID NO:36). When ectopically expressed, this gene will produce a fluorescent protein due to its unique ability to independently form a chromophore (Chalfie et al., Gene (1992) 111:229-233). This finding has enabled broad applications for the use of GFP in cell biology as a genetically encoded fluorescent label.

Genes encoding fluorescent proteins have since been cloned from organisms of a wide variety of different phylogenetic clades including, but not limited to: Hydrozoa, Anthozoa, Arthropoda (Copepoda) and Chordrata (Brachiostoma), e.g., as reported in: Matz et al., Nat. Biotechnol. (1999) 17: 969-973; Chudakov et al., Trends Biotechnol. (2005) 23: 605-613; Shagin et al., Mol. Biol. Evol. (2004) 21: 841-850; Masuda et al., Gene (2006) 372: 18-25; Deheyn et al., Biol. Bull. (2007) 213: 95-100; and Baumann et al., Biol. Direct. (2008) 3: 28. Currently, the fluorescent protein (FP) family (also referred to in the art as the "GFP family") includes hundreds of member proteins. While these proteins may collectively be referred to as members of the "GFP family", emission maxima may vary widely in terms of wavelength, and therefore not all members of the family fluoresce green.

Proteins of the GFP family share a common GFP-like domain. This domain can be easily identified in the amino acid sequences of the various family members using available software for the analysis of protein domain organization, e.g., by using the Conserved Domain Database (CDD) program available at the website formed by placed "http://www." in front of "ncbi.nlm.nih.gov/Structure/cdd/" and the Simple Modular Architecture Research Tool (SMART) program available at the website formed by placing "http://smart." in front of "embl-heidelberg.de/". For example, the GFP-like domain of avGFP begins at amino acid residue 6 and ends at amino acid residue 229. It has been demonstrated that a core domain within this domain, the "minimum GFP-like domain," produced by truncating the protein at the N-terminus (up to 9 amino acid residues) and C-terminus (up to 11 amino acid residues) is sufficient to provide for maturation and fluorescence of GFP family proteins (Shimozono et al., Biochemistry. 2006; 45(20): 6267-71). Thus, when expressed, both GFP-like domain polypeptides and minimum GFP-like domain polypeptides can produce a protein that exhibits fluorescence.

The GFP-like domain comprises a chromophore, that is responsible for the fluorescence emitted by fluorescent proteins upon irradiation with excitation light at an appropriate wavelength. The chromophore is formed by amino acids corresponding to the Ser65-Tyr66-Gly67 region of avGFP. Corresponding amino acids in fluorescent proteins other than avGFP can be determined by aligning the amino acid sequence of a protein under examination with avGFP (SEQ ID NO:36), e.g., as described in Matz et al., Nat. Biotechnol. (1999) 17: 969-973. As used herein the term "fluorescent protein" or "fluoroprotein" means a protein that is fluorescent; e.g., it may exhibit low, medium or intense fluorescence upon irradiation with light of the appropriate excitation wavelength. The fluorescent proteins of the present invention do not include proteins that exhibit fluorescence only from residues that act by themselves as intrinsic fluors, i.e., tryptophan, tyrosine and phenylalanine. As used herein, the term "fluorescent protein" also does not include luciferases, such as *Renilla* luciferase.

In fluorescent proteins of the GFP family, the chromophore is formed autocatalytically, i.e. no enzymes, cofactors and/or substrates are required for chromophore formation and fluorescence with the exception of molecular oxygen. It has been demonstrated that the green chromophore in GFP is formed by cyclization of the protein backbone in the Ser65-Tyr66-Gly67 region, followed by dehydrogenation of the $C\alpha$-$C\beta$ bond of Tyr66. As a result, a bicyclic structure of 5-(4-hydroxybenzylidene)-3,5-dihydro-4H-imidazol-4-one is formed, in which the six-member aromatic ring of the Tyr66 side chain is linked to an unusual five-member heterocycle, which itself originates from condensation of the carbonyl carbon of Ser65 with the nitrogen of Gly67 (see e.g., Heim et al., Proc Nat'l Acad. Sci USA. (1994) 91:12501-12504; Ormo et al., Science (1996) 273:1392-1395; and Yang et al., Nat. Biotechnol. (1996) 14:1246-1251). All of the green proteins possess the avGFP-like chromophore, with modifications of protein's environment contributing to differences in the spectral shapes of these different proteins (see e.g., Brejc et al., Proc. Nat'l Acad. Sci. USA (1997) 94: 2306-2311; Palm et al., Nat. Struct. Biol. (1997) 4:361-365; and Gurskaya et al., BMC Biochem. (2001) 2:6).

In red GFP-like proteins, additional chemical modification of the GFP-like chromophore occurs. In particular, oxidation of a $C\alpha$-N bond at residue 65 (avGFP numbering) results in an acylimine group conjugated to a GFP-like core in DsRed (SEQ ID NO:37) (see Gross et al., Proc. Nat'l Acad. Sci. USA (2000) 97:11990-11995; Wall et al., Nat. Struct. Biol. (2000) 7:1133-1138; and Yarbrough et al., Proc. Nat'l Acad. Sci. USA (2001) 98:462-467). The DsRed-like chromophore is formed within many other proteins with red-shifted absorption and fluorescence (See e.g., Pakhomov, A. A. and Martynov, V. I., Chem. Biol. (2008) 15: 755-764). In some proteins, the acylimine moiety of the DsRed chromophore is further attacked by various nucleophiles to form additional types of red-shifted chromophores. For example, the chromophore in the purple chromoprotein asFP595 is formed by hydrolysis of the acylimine group, resulting in cleavage of the protein backbone and formation of a keto group conjugated to a GFP-like chromophore core (see e.g., Quillin et al., Biochemistry (2005) 44: 5774-5787; and Yampolsky et al., Biochemistry (2005) 44: 5788-5793). In the orange fluorescent proteins mOrange and mKO, nucleophilic addition of Thr65 (in mOrange) or Cys65 (in mKO) side chain groups leads to unusual heterocycles without protein backbone scission (see e.g., Shu et al., Biochemistry (2006) 45: 9639-9647 and Kikuchi et al., Biochemistry (2008) 47: 11573-11580). Thus, amino acid substitution of one or more residues in the chromophore and chromophore environment will strongly affect fluorescence maxima of FPs. These positions crucial for fluorescence of particular color can be found by sequence comparison of fluorescent proteins of different colors. In many cases, one amino acid substitution, i.e. corresponding to residue 65 of avGFP, is required to produce a green fluorescent protein from the red FP (see e.g., Gurskaya et al., BMC Biochemistry (2001) 2:6).

The three-dimensional structure of the GFP-like domain represents a so-called β-can, a 11-stranded β-barrel enclosing an α-helix (see e.g., Ormo et al., Science (1996) 273: 1392-1395; Wall et al., Nat. Struct. Biol. (2000), 7: 1133-1138; Yarbrough et al., Proc. Nat'l Acad. Sci. USA (2001) 98: 462-467; Prescott et al., Structure (Camb) (2003) 11: 275-284; Petersen et al., J. Biol. Chem. (2003) 278: 44626-44631; Wilmann et al., J. Biol Chem (2005), 280: 2401-2404; Remington et al., Biochemistry (2005) 44: 202-212; and Quillin et al., Biochemistry (2005) 44: 5774-5787). The chromophore is located in the central region of the α-helix.

Fluorescent proteins of the GFP family display varying degrees of quaternary structure. avGFP and its derivatives may dimerize at high concentration, e.g. when overexpressed alone or as fusion proteins, or when immobilized at high concentrations, such as when constrained to membranes or when incorporated as fusion proteins to form biopolymers (Campbell et al., Proc. Natl. Acad. Sci. U.S.A., 2002, 99, 7877-7882; Zacharias et al., Science, 2002, 296, 913-916). *Renilla* sea pansies FPs have been verified to form obligate dimers, which are necessary for solubility (Ward, in Green Fluorescent Protein: Properties, Applications, and Protocols, ed. M. Chalfie and S. R. Kain, Wiley-Interscience, New York, 2nd edn, 2006, pp. 39-65). Most Anthozoan fluorescent proteins form tetramers at physiological concentrations (Campbell et al., Proc. Natl. Acad. Sci. U.S.A., 2002, 99, 7877-7882). Strict tetramerization motifs are common for several native yellow, orange, and red fluorescent proteins isolated in reef corals and anemones (Baird et al., Proc. Natl. Acad. Sci. U.S.A., 2000, 97, 11984-11989; Gross et al. Proc. Natl. Acad. Sci. U.S.A., 2000, 97, 11990-11995; Verkhusha and K. A. Lukyanov, Nat. Biotechnol., 2004, 22, 289-296; Yarbrough et al., Proc. Natl. Acad. Sci. U.S.A., 2001, 98, 462-467).

Fluorescent protein oligomerization, i.e. the formation of quaternary structures as described above, can be a significant problem for many applications in cell biology, particularly in cases where the FP is fused to a partner host protein that is targeted at a specific subcellular location. The formation of dimers and higher order oligomers induced by the FP portion of the chimera can produce atypical localization, disrupt normal function, interfere with signaling cascades, and/or restrict the fusion product to aggregation within a specific organelle or the cytoplasm. This effect is particularly evident when the FP is fused to partners such as actin, tubulin, gap junction connexins, or histones, which naturally form oligomeric structures in vivo. Fusion products with proteins that form only weak dimers may not exhibit aggregation or improper targeting, provided the localized concentration remains low. However, when dimeric FPs are targeted to specific cellular compartments, such as the tight, two-dimensional constraints of the plasma membrane, the localized FP concentration can become high enough to promote dimerization in some circumstances (Day and Davidson, Chem. Soc. Rev., 2009, 38, 2887-2921).

Fluorescent proteins are widely known today due to their use as fluorescent markers in biomedical sciences (see, e.g., detailed discussions in Lippincott-Schwartz and Patterson in Science (2003; 300(5616):87-91) and Stepanenko et al. in Curr Protein Pept Sci. (2008; 9(4):338-369)). They are applied for wide range of applications including the study of gene expression and protein localization (Chalfie et al., Science 263 (1994), 802-805, and Heim et al. in Proc. Nat. Acad. Sci. (1994), 91: 12501-12504), as a tool for visualizing subcellular organelles in cells (Rizzuto et al., Curr. Biology (1995), 5: 635-642), and for the visualization of protein localization and transport along the secretory pathway (Kaether and Gerdes, FEBS Letters (1995), 369: 267-271), etc.

For fluorescent proteins suitable for such uses, novel fluorescent proteins have been identified with improved fluorescence intensity and maturation rates at physiological temperatures, modified excitation and emission spectra, and reduce oligomerization and aggregation properties. In addition, mutagenesis of known proteins has been undertaken to improve their chemical properties. Finally, codon usage may be optimized for high expression in the desired heterological system, for example in mammalian cells (Haas, et al., Current Biology (1996), 6: 315-324; Yang, et al., Nucleic Acids Research (1996), 24: 4592-4593).

For example, novel wild type and mutagenized red and far-red fluorescent proteins are important tools for multicolor labeling techniques (Chudakov et al., Trends Biotechnol. 2005; 23(12):605-613), enhanced FRET (fluorescent resonance energy transfer) techniques (Chudakov et al., Trends Biotechnol. 2005; 23(12):605-613) and visualization in living tissues (Shcherbo et al., Nat Methods. 2007; 4(9): 741-746; Shcherbo et al., Biochem J. 2009; 418(3): 567-74; Hoffman, Trends Biotechnol. 2008, 26(1): 1-4; Deliolanis et al., J Biomed Opt. 2008, 13(4): 044008). Monomeric red and far-red fluorescent proteins are particularly important since they allow the multicolor labeling of various proteins of interest in living cells (Chudakov et al., Trends Biotechnol. 2005; 23(12):605-613).

Among far-red fluorescent proteins developed to date, mKate2 is the brightest one, and demonstrates advantageous characteristics including high pH stability, photostability, and fast maturation (Shcherbo et al., Biochem J. 2009; 418(3): 567-74). mKate2 was produced on the basis of *Entacmaea quadricolor* EqFP578 protein (U.S. Pat. No. 7,638,615) and comprises several amino acid substitutions altering its hydrophobic and hydrophilic interfaces. mKate2 has the following spectral and biochemical characteristics: excitation maximum 588 nm; emission maximum 633 nm, quantum yield 0.4 (at pH 7.5), extinction coefficient 62,500 $M^{-1}$ $cm^{-1}$ (at pH 7.5), calculated brightness 25.0 (product of extinction coefficient and quantum yield, divided by 1000), and pKa 5.4 (Shcherbo et al., Biochem J. 2009; 418(3): 567-74).

mKate2 behaves as monomer in gel filtration (size exclusion) performed using low pressure liquid chromatography (LPLC), as reported by Shcherbo et al. (Shcherbo et al., Biochem J. 2009; 418(3): 567-74). However, mKate2 is capable of dimerization, which can be detected using gel filtration (size exclusion chromatography) performed using fast protein liquid chromatography (FPLC). This dimerization can alter the activity of proteins of interest that are fused to mKate2.

SUMMARY OF THE INVENTION

Nucleic acid molecules encoding improved fluorescent mutants of the mKate2 protein, variants and derivatives thereof are provided, as well as proteins and peptides encoded by these nucleic acids. Also provided are proteins that are substantially similar to, or derivatives, homologues, or mutants of, the above-referenced specific proteins. Also provided are fragments of the nucleic acids and the peptides encoded thereby, as well as antibodies specific to the proteins and peptides of the invention. In addition, host-cells, stable cell lines and transgenic organisms comprising above-referenced nucleic acid molecules are provided.

Aspects of the invention include a nucleic acid that encodes a protein that comprises a GFP-like domain, where the GFP-like domain encodes sequence that forms a three-dimensional structure called a β-can and a functional chromophore, i.e. produces fluorescence or color. In some embodiments, the protein has a substantially reduced tendency to form dimers as compared with SEQ ID NO:2 (mKate2).

In some embodiments, the fluorescent protein comprises at least one amino acid substitution located at amino acid positions corresponding to R158, K176, Y195, or L225 of SEQ ID NO:2. In some embodiments, the fluorescent protein comprises at least two, at least three, or at least four amino acid substitutions at positions corresponding to R158, K176, Y195, and/or L225 of SEQ ID NO:2. In some embodiments, the substitution is R158A, R158S, R158D, R158N, R158G, K176E, K176N, K176D, K176S; Y195N, Y195D, Y195V, Y195A, Y195T, Y195E, Y195S, Y195C, Y195G; L225G, L225E, L225A, L225T, or L225N as compared with SEQ ID NO:2. In some embodiments the substitution is R158A, K176E, Y195N, and/or L225G. In some embodiments, the fluorescent protein has a substituted C-terminus; that is, the C-terminal amino acids corresponding to amino acids 223-232 of SEQ ID NO:2 are replaced with another sequence. In some embodiments, that sequence that is used to substitute the C-terminal amino acids is STGGAGDGGK (SEQ ID NO:31).

In some embodiments, the fluorescent protein comprises at least one amino acid substitution that enhances protein folding. In some embodiments, the substitution that enhances protein folding is a substitution at an amino acid position corresponding to H11, A46, N72, T74, Q75, I122, S129, T147, L148, K186, or K208 of SEQ ID NO:2. In some embodiments, the substitution is H11P, A46V, A46G, A46S, N72K, T74P, T74G, T74S, Q75P, I122V, I122A, S129A, T147G, T147S, L148M, K186T, K208N, K208S, K208G, or K208D.

In some embodiments, the fluorescent protein comprises at least one amino acid substitution at an amino acid position structurally close to or within the chromophore. In some embodiments, the substitution close to or within the chromophore is a substitution corresponding to L14, S29, M42, S62, F63, M64, Y65, K68, Q107, S144, A159, C173, R198, L200, Q214, E216 of SEQ ID NO:2. In some embodiments, the substitution is L14V, L14E, S29G, S29T, S29A, M42A, M42T, M42S, M42C, M42N, S62G, S62A, S62T, S62C, S62V, F63C, F63I, M64C, M64Y, M64T, M64Q, M64G, M64S, M64L, Y65W, Y65H, Y65L, K68R, Q107E, Q107D, Q107N, S144G, S144A, S144C, S144V, S144T, S144N, S144F, S144H, A159C, A159S, A159G, A159T, A159M, A159N, C173A, C173S, C173G, R198Y, R198E, R198G, R198I, L200S, Q214E, Q214L, E216Q.

In some embodiments, the GFP-like domain of the fluorescent protein shares 85% or more sequence identity with the minimum GFP-like domain of the fluorescent protein selected from the group consisting of SEQ ID NO:2, 4, 6, 8, 10, 12, 14, 16, 18, 20, 22, 24, 26, 28, 30, 33, 35 and 39, i.e. residues 8-221 of any of SEQ ID NO:2, 4, 6, 8, 10, 12, 14, 16, 18, 20, 22, 24, 26, 28, 30, 33, 35 and 39. In some embodiments, the GFP-like domain shares 90% or more identity, 91%, 92%, 93%, 94%, 95% or more identity, i.e. 96%, 97%, 98%, 99% or more (e.g. 100%) sequence identity to the GFP-like domain of a protein selected from the group consisting of SEQ ID NO:2, 4, 6, 8, 10, 12, 14, 16, 18, 20, 22, 24, 26, 28, 30, 33, 35, and 39.

In some embodiments, the fluorescent protein has a sequence identity of 85% or more to full length fluorescent protein selected from the group consisting of SEQ ID NO:2, 4, 6, 8, 10, 12, 14, 16, 18, 20, 22, 24, 26, 28, 30, 33, 35, and 39. In some embodiments, the protein shares 90% or more identity, 91%, 92%, 93%, 94%, 95% or more identity, i.e. 96%, 97%, 98%, 99% or more (e.g. 100%) sequence identity to fluorescent protein selected from the group consisting of SEQ ID NO:2, 4, 6, 8, 10, 12, 14, 16, 18, 20, 22, 24, 26, 28, 30, 33, 35 and 39. In some embodiments, the fluorescent protein has an amino acid sequence represented by SEQ ID NO: 4, 6, 8, 10, 12, 14, 16, 18, 20, 22, 24, 26, 28, 30, 33, 35 or 39. In some embodiments, the nucleic acid encoding the fluorescent protein has a nucleotide sequence represented by SEQ ID NO: 3, 5, 7, 9, 11, 13, 15, 17, 19, 21, 23, 25, 27, 29, 32, 34 or 38.

In some embodiment the fluorescent protein comprises a substitution that provides for at least one altered spectral or biochemical property as compared with SEQ ID NO:2, wherein the property is oligomerization capacity, pH stability, photostability, absorbance spectrum, fluorescence excitation spectrum, fluorescence emission spectrum, fluorescence brightness, protein folding, and/or chromophore maturation rate.

Additional aspects of the invention include proteins that are encoded by the subject nucleic acids. In some embodiments, the protein comprises a GFP-like domain, where the GFP-like domain comprises a functional chromophore, i.e. produces fluorescence or color, and forms a β-can three-dimensional structure. In some embodiments, the protein has a substantially reduced tendency to form dimers as compared with SEQ ID NO:2.

In some embodiments, the fluorescent protein comprises at least one amino acid substitution located at amino acid position corresponding to R158, K176, Y195, or L225 of SEQ ID NO:2. In some embodiments, the fluorescent protein comprises at least two, at least three, or at least four amino acid substitutions at positions corresponding to R158, K176, Y195, and/or L225 of SEQ ID NO:2. In some embodiments, the substitution is R158A, R158S, R158D, R158N, R158G, K176E, K176N, K176D, K176S; Y195N, Y195D, Y195V, Y195A, Y195T, Y195E, Y195S, Y195C, Y195G; L225G, L225E, L225A, L225T, or L225N. In some embodiments the substitution is R158A, K176E, Y195N, and/or L225G.

In some embodiments, the fluorescent protein has a substituted C-terminus; that is, the C-terminal amino acids corresponding to amino acids 223-232 of SEQ ID NO:2 are replaced with another sequence. In some embodiments, that sequence that is used to substitute the C-terminal amino acids is STGGAGDGGK (SEQ ID NO:31).

In some embodiments, the GFP-like domain of the fluorescent protein shares 85% or more sequence identity with the minimum GFP-like domain of the fluorescent protein selected from the group consisting of SEQ ID NO:2, 4, 6, 8, 10, 12, 14, 16, 18, 20, 22, 24, 26, 28, 30, 33, 35 and 39, i.e. residues 8-221 of the fluorescent protein selected from the group consisting of SEQ ID NO:2, 4, 6, 8, 10, 12, 14, 16, 18, 20, 22, 24, 26, 28, 30, 33, 35 and 39. In some embodiments, the GFP-like domain shares 90% or more identity, 91%, 92%, 93%, 94%, 95% or more identity, i.e. 96%, 97%, 98%, 99% or more (e.g. 100%) sequence identity to the GFP-like domain of the fluorescent protein selected from the group consisting of SEQ ID NO:2, 4, 6, 8, 10, 12, 14, 16, 18, 20, 22, 24, 26, 28, 30, 33, 35 and 39.

In some embodiments, the fluorescent protein has a sequence identity of 85% or more to full length fluorescent protein selected from the group consisting of SEQ ID NO:2, 4, 6, 8, 10, 12, 14, 16, 18, 20, 22, 24, 26, 28, 30, 33, 35 and 39. In some embodiments, the protein shares 90% or more identity, 91%, 92%, 93%, 94%, 95% or more identity, i.e. 96%, 97%, 98%, 99% or more (e.g. 100%) sequence identity to the fluorescent protein selected from the group consisting of SEQ ID NO:2, 4, 6, 8, 10, 12, 14, 16, 18, 20, 22, 24, 26, 28, 30, 33, 35 and 39. In some embodiments, the fluorescent protein has an amino acid sequence represented by SEQ ID NO: 4, 6, 8, 10, 12, 14, 16, 18, 20, 22, 24, 26, 28, 30, 33, 35 or 39.

Additional aspects of the invention include vectors containing the nucleic acids of the present invention. Included also are expression cassettes comprising a nucleic acid of the present invention and regulatory elements necessary for expression of the nucleic acid in the desired host-cell. Included also are fusion proteins and nucleic acids encoding the same comprising the subject fluorescent protein or mutant thereof.

Additional aspects of the invention include methods of producing a subject fluorescent protein, by expressing of a protein in a suitable host cell and isolating the protein from that cell. In some embodiments, the method includes the steps of (a) contacting a host cell with a nucleic acid molecule of the present invention operably linked to one or more expression regulatory elements, (b) expressing the fluorescent protein from the nucleic acid molecule, and (c) isolating the protein substantially free from other proteins.

In addition, antibodies specifically binding to the proteins of the present invention or fragments thereof are provided.

Additionally, host-cells, stable cell lines, transgenic animals and transgenic plants comprising nucleic acids, vectors or expression cassettes of the present invention are provided.

Also provided are methods that use a fluorescent protein of the present invention or the nucleic acid encoding it.

Additionally, kits comprising nucleic acids or vectors or expression cassettes harboring the nucleic acids, or proteins of the present invention are provided.

BRIEF DESCRIPTION OF THE DRAWINGS

FIG. 1 shows multiple sequence alignments of exemplary novel fluorescent proteins with mKate2 (SEQ ID NO: 2), avGFP (SEQ ID NO: 36) and DsRed2 (SEQ ID No: 37). Introduced gaps are shown by dots. Conservative amino acids are marked by black. GFP-like domain start and finish are specified at the top by square brackets ("[" and "]") Amino acid residues that form chromophore is marked by pluses ("+++").

DETAILED DESCRIPTION

Figure 2:
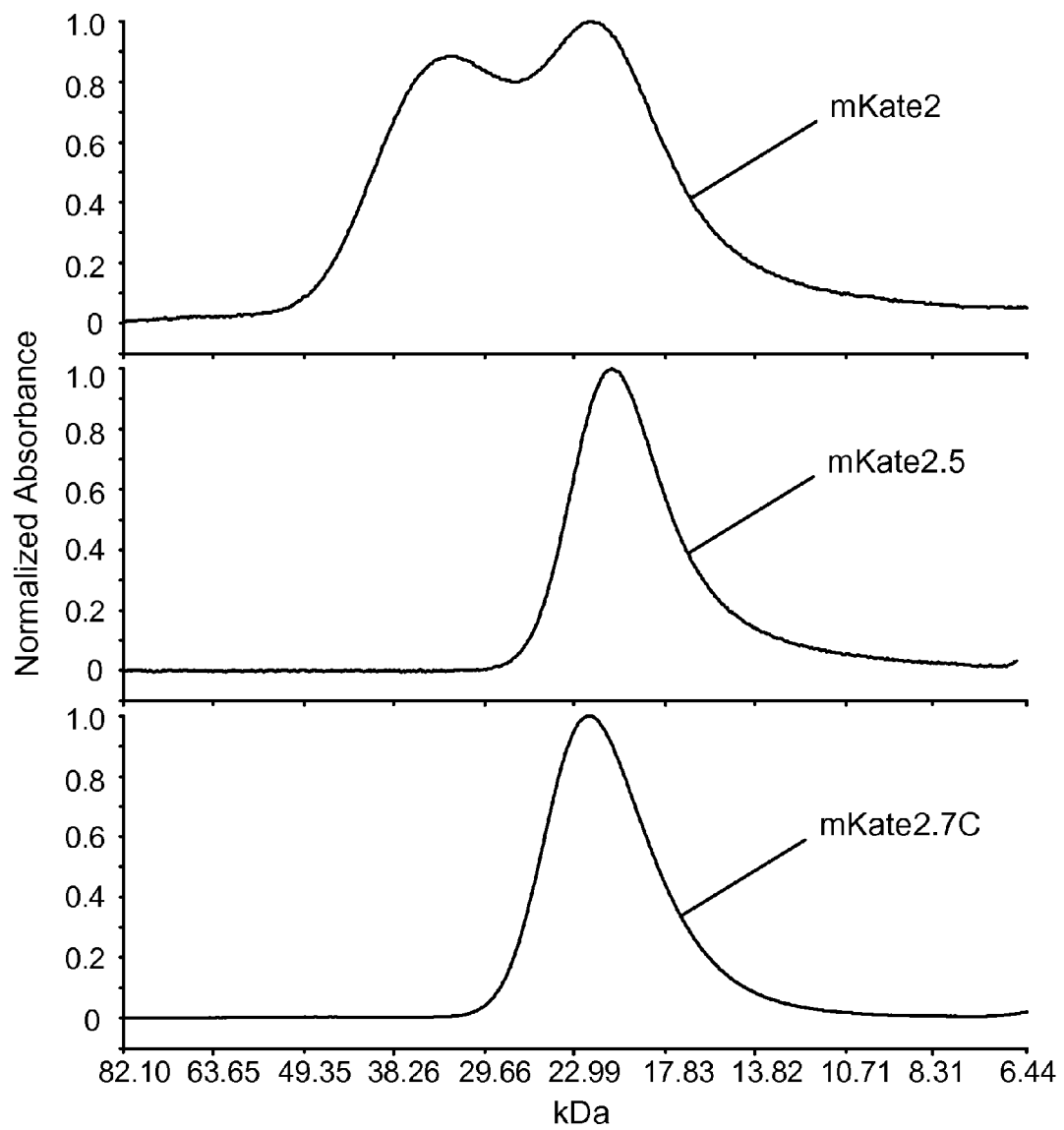
FIG. 2 shows results of fast protein liquid chromatography (FPLC) of selected fluorescent proteins. Gel filtration chromatography was performed using a Superdex 200 10/300 GL column (Amersham Biosciences), equilibrated with 40 mm Tris-HCl (pH 7.5), 150 mm NaCl buffer at a flow rate of 0.4 ml/min. Apparent molecular masses were calculated by interpolating an elution volume versus log (molecular mass) calibration curve using ferritin (440 kDa), catalase (232 kDa), aldolase (158 kDa), BSA (67 kDa), ovalbumin (43 kDa), chymotrypsinogen A (25 kDa), and ribonuclease A (13.7 kDa). 200 uL of each fluorescent protein at concentration 1 mg/ml were loaded.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the subject invention is directed to nucleic acid molecules encoding improved fluorescent mutants of the mKate2 protein, variants and derivatives thereof, and proteins and peptides encoded by these nucleic acids. Also provided are vectors and expression cassettes comprising these nucleic acids, and stable cell lines, transgenic animals, and transgenic plants comprising these nucleic acids, vectors or expression cassettes. Also provided are methods of producing these fluorescent proteins and mutants thereof, and antibodies specifically binding to these fluorescent proteins and mutants or fragments thereof. Also provided are methods that use a fluorescent protein of the present invention or the nucleic acid encoding it. Additionally, kits comprising nucleic acids or vectors or expression cassettes harboring the nucleic acids, or proteins of the present invention are provided.

Nucleic Acid Molecules

The present invention provides nucleic acid molecules that comprise nucleotide sequences encoding fluorescent mutants of mKate2 protein. A nucleic acid molecule as used herein is DNA molecules, such as genomic DNA molecules or cDNA molecules, or RNA molecules, such as mRNA molecules. In particular, the nucleic acid molecule is a cDNA molecule having an open reading frame that encodes a fluorescent protein of the invention and is capable, under appropriate conditions, of being expressed as a fluorescent protein according to the invention. The invention also encompasses nucleic acids that are homologous, substantially similar to, identical to, derived from, or mimetics of the nucleic acids encoding proteins of the present invention. The subject nucleic acids are present in an environment other than their natural environment; e.g., they are isolated, present in enriched amounts, or are present or expressed in vitro or in a cell or organism other than their naturally occurring environment.

Specific nucleic acid molecules of interest include nucleic acid molecules that encode the following fluorescent proteins, and homologs/derivates/mutants thereof (see Table 1 for more details): mKate2M1 (SEQ ID NO:4); pH-Redder-0.1 (SEQ ID NO:6); mKate2M1pHsens1 (SEQ ID NO:8); mKate2M1fold1 (SEQ ID NO:10); mKate2M1fold2 (SEQ ID NO:12); mKate2M1stab1 (SEQ ID NO:14); mKate2M1stab2 (SEQ ID NO:16); mKate2M1farred1 (SEQ ID NO:18); mKate2M1farred2 (SEQ ID NO:20); mKate2M1farred3 (SEQ ID NO:22); mKate2M1orange1 (SEQ ID NO:24), mKate2M1photo1 (SEQ ID NO:26), mKate2.5 (SEQ ID NO:28), mKate2.6 (SEQ ID NO: 39), mKate2.7C (SEQ ID NO:30), mKate2.7C-PA1 (SEQ ID NO:33), mKate2.7C-PA2 (SEQ ID NO:35). The deduced cDNA coding sequences for these proteins are the following: mKate2M1 (SEQ ID NO:3); pH-Redder-0.1 (SEQ ID NO:5); mKate2M1pHsens1 (SEQ ID NO:7); mKate2M1fold1 (SEQ ID NO:9); mKate2M1fold2 (SEQ ID NO:11); mKate2M1stab1 (SEQ ID NO:13); mKate2M1stab2 (SEQ ID NO:15); mKate2M1farred1 (SEQ ID NO:17); mKate2M1farred2 (SEQ ID NO:19); mKate2M1farred3 (SEQ ID NO:21); mKate2M1orange1 (SEQ ID NO:23), mKate2M1photo1 (SEQ ID NO:25), mKate2.5 (SEQ ID NO:27), mKate2.7C (SEQ ID NO:29), mKate2.6 (SEQ ID NO: 38), mKate2.7C-PA1 (SEQ ID NO:32), and mKate2.7C-PA2 (SEQ ID NO:34). Each of these particular types of nucleic acid molecules of interest is discussed below and in the experimental section.

In addition to the above described specific nucleic acid compositions, also of interest are homologues of the above sequences. With respect to homologues of the subject nucleic acids, the source of homologous genes may be any species of plant or animal or the sequence may be wholly or partially synthetic (e.g. genetically engineered). In certain embodiments, sequence similarity between homologues is at least about 20%, sometimes at least about 25%, and may be 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence will usually be at least about 18 contiguous nucleotides long, more usually at least about 30 contiguous nucleotides long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17). The sequences provided herein are essential for recognizing related and homologous nucleic acids in database searches. Also of interest are nucleic acids of substantially the same length as the nucleic acid identified as SEQ ID NOS:3, 5, 7, 9, 11, 13, 15, 17, 19, 21, 23, 25, 27, 29, 32, and 34, where by substantially the same length is meant that any difference in length does not exceed about 10%, usually does not exceed about 5% and more usually does not exceed about 2%; and have sequence identity to any of these sequences of about 90% or more, usually at least about 95% and more, usually at least about 99% over the entire length of the nucleic acid. In many embodiments, the nucleic acids have a sequence that is substantially similar (i.e. the same as) or identical to the sequences of SEQ ID NOS:3, 5, 7, 9, 11, 13, 15, 17, 19, 21, 23, 25, 27, 29, 32, and 34. By substantially similar is meant that sequence identity will generally be at least about 90%, usually at least about 95% and often at least about 96%, 97%, 98%, or even 99%.

Mutants or derivates can be generated on a template nucleic acid selected from the described-above nucleic acids by modifying, deleting or adding one or more nucleotides in the template sequence, or a combination thereof, to generate a variant of the template nucleic acid. The modifications, additions or deletions can be introduced by any convenient method, including error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-directed mutagenesis, random mutagenesis, gene reassembly, gene site saturated mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and combinations thereof (see, for example, Gustin et al., Biotechniques (1993) 14: 22; Barany, Gene (1985) 37: 111-123; Colicelli et al., Mol. Gen. Genet. (1985) 199:537-539; and Sambrook et al., Molecular Cloning: A Laboratory Manual, (1989), CSH Press, pp. 15.3-15.108). The fluorescent proteins encoded by mutant or derived nucleic acids may have the same fluorescent or biochemical properties as the initial fluorescent protein. Alternatively, the mutant or derived nucleic acids may encode fluorescent proteins with altered properties, e.g., they can have altered photostability, oligomerization state, excitation and emission spectra, quantum yield, extinction coefficient.

In addition, degenerate variants of the nucleic acids that encode the proteins of the present invention are also provided. Degenerate variants of nucleic acids are nucleic acids in which the amino-acid encoding codons are replaced with other codons encoding the same amino acids. For example, degenerate variants of a nucleic acid are generated to increase its expression in a host cell. In this embodiment, codons of the nucleic acid that are non-preferred or are less preferred in the host cell are replaced with the codons over-represented in coding sequences in genes in the host cell, wherein the replaced codons encodes the same amino acid. Humanized versions of the nucleic acids of the present invention are under particular interest. As used herein, the term "humanized" refers to changes made to the nucleic acid sequence to optimize the codons for expression of the protein in mammalian (human) cells (Yang et al., Nucleic Acids Research (1996) 24: 4592-4593). See also U.S. Pat. No. 5,795,737 which describes humanization of proteins, the disclosure of which is herein incorporated by reference. Examples of degenerated variants of interest are described in more details in experimental part, infra.

The term "cDNA" as used herein is intended to include nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the protein.

A genomic sequence of interest may comprise the nucleic acid present between the initiation codon and the stop codon, as defined in the listed sequences, including all of the introns that are normally present in a native chromosome. The genomic sequence of interest further may include 5' an 3' non-translated regions found in the mature mRNA, as well as specific transcriptional and translational regulatory sequences, such as promoters, enhancers, etc., including about 1 kb, but possibly more, of flanking genomic DNA at either the 5' or 3' end of the transcribed region.

The nucleic acid molecules of the invention may encode all or a part of the fluorescent proteins having amino acid sequences represented by SEQ ID NOs: 4, 6, 8, 10, 12, 14, 16, 18, 20, 22, 24, 26, 28, 30, 33, 35 or 39 or mutants thereof. In certain embodiments, the nucleic acid molecules encodes complete or truncated (minimum) GFP-like domains of the subject proteins that are capable to be fluorescent when expressed in vitro and\or in vivo. GFP-like domains are described further below.

Double- or single-stranded fragments may be obtained from the DNA sequence by chemically synthesizing oligonucleotides in accordance with conventional methods, by restriction enzyme digestion, by PCR amplification, etc. For the most part, DNA fragments will be at least about 15 nucleotides in length, usually at least about 18 nucleotides in length or about 25 nucleotides in length, and may be at least about 50 nucleotides in length, about 100, about 200, about 300, about 400, about 500, about 600, about 700 contiguous nucleotides or greater in length (e.g. 642 bp or 660 bp long). The DNA fragment may share 50%, 55%, 60%, 65%, 70%, 75% or more sequence identity with a fragment of the subject nucleic acid, e.g. 80%, 85%, or 90% or more identity, more often 92%, 95%, 96%, 97%, 99% or more, e.g. 100% identity with a fragment of the subject nucleic acid that is about 15 contiguous nucleotides in length, about 18 contiguous nucleotides in length, about 25 contiguous nucleotides in length, about 50 contiguous nucleotides in length, or about 100, about 200, about 300, about 400, about 500, about 600, or about 700 contiguous nucleotides or greater in length.

The subject nucleic acids may encode fragments of the subject proteins or the full-length proteins; e.g., the subject nucleic acids may encode polypeptides of about 25 amino acids, about 50, about 75, about 100, about 125, about 150, about 200 amino acids, 214 amino acids; 215 amino acids; 217 amino acids; 218 amino acids; 219 amino acids; 220 amino acids; up to the full length protein.

The subject nucleic acids may be isolated and obtained in substantially purified form. Substantially purified form means that the nucleic acids are at least about 80% pure, usually at least about 90% pure and are typically "recombinant", i.e., flanked by one or more nucleotides with which they are not normally associated on a naturally-occurring chromosome in a natural host organism.

The nucleic acids of the present invention, e.g. the corresponding cDNAs, full-length genes and constructs can be generated synthetically by a number of different protocols known to those of skill in the art. Appropriate nucleic acid constructs are purified using standard recombinant DNA techniques as described in, for example, Sambrook et al., Molecular Cloning: A Laboratory Manual, 2nd Ed., (1989) Cold Spring Harbor Press, Cold Spring Harbor, N.Y., and under regulations described in, e.g., United States Dept. of HHS, National Institute of Health (NIH) Guidelines for Recombinant DNA Research.

Also provided are nucleic acids that encode fusion proteins comprising a fluorescent protein of the present invention that are discussed in more details below.

Also provided are vectors and other nucleic acid constructs comprising the subject nucleic acids. Suitable vectors include viral and non-viral vectors, plasmids, cosmids, phages, etc., preferably plasmids, and used for cloning, amplifying, expressing, transferring etc. of the nucleic acid sequence of the present invention in the appropriate host. The choice of appropriate vector is well within the skill of the art, and many such vectors are available commercially. To prepare the constructs, the partial or full-length nucleic acid is inserted into a vector typically by means of DNA ligase attachment to a cleaved restriction enzyme site in the vector. Alternatively, the desired nucleotide sequence can be inserted by homologous recombination in vivo, typically by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems used inter alia for the production of the subject fluorescent proteins or fusion proteins thereof or for replication of the subject nucleic acid molecules. The expression cassette may exist as an extrachromosomal element or may be integrated into the genome of the cell as a result of introduction of the expression cassette into the cell. For expression, the gene product encoded by the nucleic acid of the invention is expressed in any convenient expression system, including, for example, bacterial, yeast, insect, amphibian, or mammalian systems. In the expression vector, a subject nucleic acid is operably linked to a regulatory sequence that can include promoters, enhancers, terminators, operators, repressors and inducers. Methods for preparing expression cassettes or systems capable of expressing the desired product are known for a person skilled in the art.

Cell lines, which stably express the proteins of present invention, can be selected by the methods known in the art (e.g. the co-transfection with a selectable marker such as dhfr, gpt, neomycin, hygromycin allows the identification and isolation of the transfected cells that contain the gene integrated into a genome).

The above-described expression systems may be used in prokaryotic or eukaryotic hosts. Host-cells such as *E. coli*, *B. subtilis*, *S. cerevisiae*, insect cells in combination with baculovirus vectors, or cells of a higher organism such as vertebrates, e.g., COS 7 cells, HEK 293, CHO, *Xenopus* oocytes, etc., may be used for production of the protein.

When any of the above-referenced host cells, or other appropriate host cells or organisms are used to replicate and/or express the nucleic acids of the invention, the resulting replicated nucleic acid, expressed protein or polypeptide is within the scope of the invention as a product of the host cell or organism. The product may be recovered by an appropriate means known in the art.

Also of interest are promoter sequences of the genomic sequences of the present invention, where the sequence of the 5' flanking region may be utilized for promoter elements, including enhancer binding sites, that, for example, provide for regulation of expression in cells/tissues where the subject proteins gene are expressed.

Also provided are small DNA fragments of the subject nucleic acids, that are useful as primers for PCR, hybridization screening probes, etc. Larger DNA fragments are useful for production of the encoded polypeptide, as described previously. However, for use in geometric amplification reactions, such as geometric PCR, a pair of small DNA fragments, i.e., primers, will be used. The exact composition of the primer sequences is not critical for the invention, but for most applications, the primers will hybridize to the subject sequence under stringent conditions, as is known in the art. It is preferable to choose a pair of primers that will generate an amplification product of at least about 50 nucleotides, preferably at least about 100 nucleotides and may extend to the complete sequence of the nucleic acid. Algorithms for the selection of primer sequences are generally known, and are available in commercial software packages. Amplification primers hybridize to complementary strands of DNA and will prime toward each other.

The nucleic acid molecules of the present invention also may be used to identify expression of a gene in a biological specimen. The manner in which one probes cells for the presence of particular nucleotide sequences, such as genomic DNA or RNA, is well established in the art. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g., nitrocellulose, nylon, etc., and then probed with a fragment of the subject DNA as a probe. Other techniques, such as oligonucleotide ligation assays, in situ hybridizations, and hybridization to DNA probes arrayed on a solid chip may also be used. Detection of mRNA hybridizing to the subject sequence is indicative of gene expression in the sample.

The subject nucleic acids, including flanking promoter regions and coding regions, may be mutated in various ways known in the art to generate targeted changes in promoter strength or to vary the sequence of the encoded protein or properties of the encoded protein, including the fluorescent properties of the encoded protein.

Proteins

Also provided by the subject invention are fluorescent proteins, derivates, and mutants thereof including full-length proteins, as well as portions or fragments thereof.

As discussed above, specific fluorescent proteins of interest include the following fluorescent proteins: mKate2M1 (SEQ ID NO:4); pH-Redder-0.1 (SEQ ID NO:6); mKate2M1pHsens1 (SEQ ID NO:8); mKate2M1fold1 (SEQ ID NO:10); mKate2M1fold2 (SEQ ID NO:12); mKate2M1stab1 (SEQ ID NO:14); mKate2M1stab2 (SEQ ID NO:16); mKate2M1farred1 (SEQ ID NO:18); mKate2M1farred2 (SEQ ID NO:20); mKate2M1farred3 (SEQ ID NO:22); mKate2M1orange1 (SEQ ID NO:24), mKate2M1photo1 (SEQ ID NO:26), mKate2.5 (SEQ ID NO:28), mKate2.6 (SEQ ID NO: 39), mKate2.7C (SEQ ID NO:30), mKate2.7C-PA1 (SEQ ID NO:33), mKate2.7C-PA2 (SEQ ID NO:35). Also of interest are mutants and fragments thereof, e.g. fragments comprising the GFP-like domain, as described further below.

Homologs that vary in sequence from the above provided specific amino acid sequences of the subject invention, i.e., SEQ ID NOs: 4, 6, 8, 10, 12, 14, 16, 18, 20, 22, 24, 26, 28, 30, 33, 35 or 39 are also provided. By homolog is meant a protein having 50% or more, usually 55% or more and more usually 60% or more amino acid sequence identity to amino acid sequences of referred protein as determined using MegAlign, DNAstar clustal algorithm as described in D. G. Higgins and P. M. Sharp, "Fast and Sensitive multiple Sequence Alignments on a Microcomputer," CABIOS, 5 pp. 151-3 (1989) (using parameters ktuple 1, gap penalty 3, window 5 and diagonals saved 5). In many embodiments, homologs of interest have much higher sequence identity e.g., 70% or more, 75% or more, 80% or more, 85% or more, 90% or more (e.g., 92% or more, 93% or more, 94% or more), e.g., 95% or more, 96% or more, 97% or more, 98% or more, 99% or more, or 99.5%, particularly for the amino acid sequence that provides the functional regions of the protein.

Also provided are proteins that are substantially identical to the proteins of SEQ ID NOs: 4, 6, 8, 10, 12, 14, 16, 18, 20, 22, 24, 26, 28, 30, 33, 35 or 39, where by substantially identical is meant that the full-length protein or fragment thereof (e.g. a complete GFP-like domain or minimum (truncated) GFP-like domain) has an amino acid sequence identity to the sequence of reference protein or fragment of 90% or more, in some instances, 92% or more, or 95% or more, where in some instances the identity may be much higher, e.g., at least 96%, at least 97%, at least 98%, at least 99% or higher.

In aspects of the invention, subject proteins and mutants thereof range in length from about 150 to 300 amino acids, more usually from about 200 to 250 amino acid residues. In aspects of the invention, the subject proteins and mutants thereof have a molecular weight ranging from about 15 to 35 kDa, more usually from about 17.5 to 32.5 kDa, where the molecular weight is the average molecular weight, i.e. the calculated molecular weight based upon the average weight for amino acids of 0.11 kD per amino acid.

In aspects of the invention, the subject proteins are bright, where by bright is meant that they exhibit fluorescence that can be detected by common methods (e.g., visual screening, spectrophotometry, spectrofluorometry, fluorescent microscopy, by FACS machines, etc.) Fluorescence brightness of particular fluorescent proteins is determined by its quantum yield multiplied by maximal extinction coefficient.

Also provided are the subject proteins and mutants thereof that demonstrate particular fluorescent, or spectral, properties. "Fluorescent property" or "spectral property" is used to refer to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties of reference protein in different conditions is useful. A measurable difference can be determined as the amount of any quantitative fluorescent property, e.g., the amount of fluorescence at a particular wavelength, or the integral of fluorescence over the emission spectrum. In some aspects, the subject proteins or mutants thereof have an absorbance maximum ranging from about 300 nm to 700 nm, usually from about 390 nm to 630 nm and more usually from about 540 to 600 nm, and often from about 550 to 600 nm, while the maximum of emission spectra of the subject proteins typically ranges from about 400 nm to 700 nm, usually from about 450 nm to 680 nm and more usually from about 550 to 670 nm while in many embodiments the maximum of emission spectra ranges from about 600 to 660 nm. The subject proteins generally have a maximum extinction coefficient that ranges from about 25,000 to 150,000 $cm^{-1}mol^{-1}$ and usually from about 45,000 to 140,000 $cm^{-1} mol^{-1}$, e.g., 50,000 to 130,000 $cm^{-1} mol^{-1}$. The subject proteins generally have a quantum yield that ranges from about 0.05 to 0.8, usually from 0.1 to 0.4, e.g. from 0.15 to 0.3. A fluorescence spectrophotometer (e.g. Varian Cary Eclipse Fluorescence Spectrophotometer, or spectrophotometer SMS 2 VIS built into the stereomicroscope Olympus SZX-12) can be used for measuring excitation-emission spectra, with wavelength corrections if appropriate.

Also provided are fluorescent proteins that possess a GFP-like domain that is homologous to the GFP-like domain of Green Fluorescent Protein from *A. victoria* (avGFP) (SEQ ID NO:36). Algorithms for sequence analysis are known in the art, such as BLAST, described in Altschul et al. (1990), J. Mol. Biol. 215:403-10 (using default settings, i.e. parameters w=4 and T=17). Alternatively, GFP-like domain can be identified in the amino acid sequences of the subject proteins using available software for analysis of domain organization, for example using Conserved Domain Database (CDD, website identifiable by placing "http://www" in front of "ncbi.nlm.nih.gov/Structure/cdd/") and Simple Modular Architecture Research Tool (SMART, website identifiable by placing "http://" in front of smart.embl-heidelberg.de/). The minimum GFP-like domain of the subject nucleic acids is that portion of the GFP-like domain that is necessary and sufficient for the protein to mature and demonstrate fluorescence. In other words, the minimum GFP-like domain is responsible for the fluorescence of the protein.

Sequence alignments of subject proteins with avGFP, DsRed can be used to identify the starts and the ends of the GFP-like domain and minimum GFP-like domain (i.e. core sequence that is necessary and sufficient for the maturation and fluorescence of the subject fluorescent proteins). Multiple alignment of the sequences can be performed using the Clustal method of alignment (Higgins and Sharp, CABIOS. 5:151153 (1989)) with default parameters (GAP PENALTY=10, GAP LENGTH PENALTY=10), unless otherwise specified. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

In aspects of the invention, the GFP-like domain of the subject protein begins at the amino acid residue corresponding to the position 6 of avGFP as identified using sequence alignment of a fluorescent protein under examination and avGFP (SEQ ID NO:36), e.g. residue 4 of SEQ ID NO:2 and mutants thereof. In some embodiments, the GFP-like domain ends at the amino acid residue corresponding to the position 229 of avGFP, e.g. residue 223 of SEQ ID NO:2 and mutants thereof. In additional aspects, the minimum GFP-like domain is a GFP-like domain that is truncated at its N-terminus, beginning, for example, at a residue corresponding to residue 8, 10, 12, or 15 of avGFP, e.g. residue 6, 8, 10, or 13 of SEQ ID NO:2 and mutants thereof. In additional aspects, the minimum GFP-like domain is a GFP-like domain that is truncated at its C-terminus, ending, for example, at a residue corresponding to residue 227, 225, 223, 220, or 215 of avGFP, e.g. residue 221, 219, 217, 214, or 209 of SEQ ID NO:2 and mutants thereof (e.g. SEQ ID NO: 4, 6, 8, 10, 12, 14, 16, 18, 20, 22, 24, 26, 28, 30, 33, 35, 39). In additional aspects, the minimum GFP-like domain is 200 amino acids long or more, more usually about 215 amino acids long, and more usually at least 219 amino acids long (e.g. 219; 220; 221; 222; 223; 224; 225; 230; 231; 232; 233 amino acids long). Accordingly, in some instances, the GFP-like domain of SEQ ID NO:2 and mutants thereof may begin, for example, at about residue 4 to about amino acid residue 223, where the minimum GFP-like domain may begin at about residue 6 and end at about residue 221, or may begin at about residue 8 and end at about residue 219. In some instances, the minimum GFP-like domain of SEQ ID NO:2 and mutants thereof extends from residue 8 to residue 221.

Also provided are proteins that have a GFP-like domain that is homologous to the GFP-like domain of fluorescent proteins of SEQ ID NOs: 2, 4, 6, 8, 10, 12, 14, 16, 18, 20, 22, 24, 26, 28, 30, 33, 35, or 39, where by homologous it is meant sharing a sequence identity that is 50% or more, 55% or more, or 60% or more with the GFP-like domain of a reference protein interest, and in some cases, having much higher sequence identity e.g., 70% or more, 75% or more, 80% or more, 85% or more, 90% or more (e.g., 91% or more, 92% or more, 93% or more, 94% or more), e.g., 95% or more, 96% or more, 97% or more, 98% or more, 99% or more, or 99.5%. In some embodiments, the proteins have a GFP-like domain that is substantially identical to the GFP-like domain of the reference protein, e.g. SEQ ID NOs: 2, 4, 6, 8, 10, 12, 14, 16, 18, 20, 22, 24, 26, 28, 30, 33, 35, or 39, where by substantially identical it is meant sharing a sequence identity to the GFP-like domain of the subject protein of at least 90% and more usually at least about 95%, where in some instances the identity may be much higher, e.g., at least 96%, at least 97%, at least 98%, at least 99% or higher.

Also provided are proteins that have a GFP-like domain that is homologous to the minimum GFP-like domain of fluorescent proteins of SEQ ID NOs: 2, 4, 6, 8, 10, 12, 14, 16, 18, 20, 22, 24, 26, 28, 30, 33, 35 or 39, where by homologous it is meant sharing a sequence identity that is 50% or more, 55% or more, or 60% or more with the GFP-like domain of a reference protein interest, and in some cases, having much higher sequence identity e.g., 70% or more, 75% or more, 80% or more, 85% or more, 90% or more (e.g., 92% or more, 93% or more, 94% or more), e.g., 95% or more, 96% or more, 97% or more, 98% or more, 99% or more, or 99.5%. In some embodiments, the proteins have a GFP-like domain that is substantially identical to the GFP-like domain of the reference protein, e.g. SEQ ID NOs: 2, 4, 6, 8, 10, 12, 14, 16, 18, 20, 22, 24, 26, 28, 30, 33, 35, or 39 where by substantially identical it is meant sharing a sequence identity to the GFP-like domain of the subject protein of at least 90% and more usually at least about 95%, where in some instances the identity may be much higher, e.g., at least 96%, at least 97%, at least 98%, at least 99% or higher.

Fluorescent proteins that are mutants and derivatives of the above-described proteins, that is, mutants or derivatives that fluoresce, i.e. emit fluorescence, are also provided. Mutations contemplated include, without limitation, substitutions, deletions or insertions of one or more amino acids. It is well known in the art that, barring substitution of the amino acid residues that are strictly conserved across members of the GFP family of proteins, e.g. some residues of the chromophore and chromophore environment (i.e. corresponding to residues 67 and 96 of avGFP), a high degree of mutation may be tolerated. For example, substitutions close to or within the chromophore, e.g. corresponding to positions L14, S29, M42, S62, F63, M64, Y65, K68, Q107, S144, A159, C173, R198, L200, Q214, E216 of SEQ ID NO:2, may be made without destroying fluorescence, for example substitutions that are L14V, L14E, S29G, S29T, S29A, M42A, M42T, M42S, M42C, M42N, S62G, S62A, S62T, S62C, S62V, F63C, F63I, M64C, M64Y, M64T, M64Q, M64G, M64S, M64L, Y65W, Y65H, Y65L, K68R, Q107E, Q107D, Q107N, S144G, S144A, S144C, S144V, S144T, S144N, S144F, S144H, A159C, A159S, A159G, A159T, A159M, A159N, C173A, C173S, C173G, R198Y, R198E, R198G, R198I, L200S, Q214E, Q214L, and/or E216Q relative to SEQ ID NO:2. As another example, and as demonstrated in the experimental section below, fluorescence is maintained upon substitution of the following amino acid residues of mKate2 either independently or in combination: 11, 42, 46, 68, 72, 74 75, 107, 122, 129, 136, 144, 147, 148, 158, 159, 176, 186, 195, 198, and 208. Other examples of residues that may be substituted may be readily identified by cross-referencing alignments made between known members of the GFP family that identify strictly conserved residues, e.g. as provided in FIG. 1 of the accompanying drawings, with the teachings of the structure for GFP disclosed in by Yang et al (1996) Nature Biotechnology 14:1246-1251, Ormo et al. (1996) Science 273:1392-1395, and Matz et al. (1999) Nature Biotechnology 17:969-973, the entire disclosures of which are incorporated herein, and by performing alignments such as that provided in FIG. 1 of the accompanying drawings.

Additional mutations contemplated include N-terminal truncations or extensions, and/or C-terminal truncations or extensions. For example, the experimental section demonstrates that C-terminal amino acids corresponding to residues 223-232 of SEQ ID NO:2 may be substituted without loss of fluorescence. Likewise, it is known in the art that proteins of the GFP family with at least 9 amino acid residues deleted at the N terminus and/or at least 11 amino acid residues deleted at the C-terminus still mature and fluoresce; see, e.g. Shimozono et al., Biochemistry. 2006; 45(20): 6267-71, the disclosure of which is incorporated by reference. In some embodiments, the fluorescent protein has a substituted C-terminus; that is, the C-terminal amino acids corresponding to amino acids 223-232 of SEQ ID NO:2 are replaced with another sequence. In some embodiments, that sequence that is used to substitute the C-terminal amino acids is STGGAGDGGK (SEQ ID NO:31).

Additional amino acid residues within and flanking the GFP-like domain and minimum GFP-like domain that may be substituted in the subject proteins without loss of fluorescence are readily identifiable by performing sequence alignments with avGFP, DsRed and other known fluorescent proteins as discussed above.

Aspects of the invention include mutants and variants which retain biological properties of the initial proteins (e.g. proteins subjected for mutagenesis). In other aspects of the invention, mutants and variants have biological properties which differ from the initial proteins. The term "biological property" of the proteins of the present invention refers to, without limitation, spectral properties, such as absorbance maximum, emission maximum, maximum extinction coefficient, brightness (e.g., as compared to the reference protein such mKate2 protein), and the like; and biochemical properties, such as in vivo and/or in vitro stability (e.g., half-life), sensitivity to pH, maturation speed, aggregation/oligomerization tendency, and other such properties.

Aspects of the invention include proteins that comprise one or more mutations that reduces the oligomerization capacity of the subject protein, e.g. a reduced tendency to dimerize as compared with SEQ ID NO:2. The difference in dimerization can be monitored in vitro for the purified protein samples, using sensitive techniques, such as fast protein liquid chromatography (FPLC), or light scattering, both performed at high concentrations of the protein (above 20 µM). The difference can not be monitored accurately using the low pressure liquid chromatography (LPLC). In some embodiments, the mutation is one or more substitutions at positions corresponding to R158, K176, Y195, and/or L225 of SEQ ID NO:2, i.e. at least one, at least two, at least three, or four substitutions at the positions corresponding to R158, K176, Y195, and/or L225 of SEQ ID NO:2. In some embodiments, the substitution is R158A, R158S, R158D, R158N, R158G, K176E, K176N, K176D, K176S; Y195N, Y195D, Y195V, Y195A, Y195T, Y195E, Y195S, Y195C, Y195G; L225G, L225E, L225A, L225T, or L225N (or 158A, 158S, 158D, 158N, 158G, 176E, 176N, 176D, 176S; 195N, 195D, 195V, 195A, 195T, 195E, 195S, 195C, 195G; 225G, 225E, 225A, 225T, or 225N, if the protein of interest is not SEQ ID NO:2, where the number is the position in the protein of interest corresponding to the position in SEQ ID NO:2, and the letter represents the amino acid that is substituted in at that position). In some embodiments, the substitution is selected from the group consisting of R158A, K176E, Y195N, and L225G (or 158A, 176E, 195N and 225G, if the protein of interest is not SEQ ID NO:2). In some embodiments, the mutation is a substitution of the C-terminal 10 amino acids, usually corresponding to amino acids 223-232 of SEQ ID NO:2. In some embodiments, the sequence that is used to substitute the C-terminal 10 amino acids (the "C' substitution sequence") is STG-GAGDGGK (SEQ ID NO:31). In some embodiments, the protein comprises both one or more substitutions (e.g. 1, 2, or 3 substitutions) at the positions R158, K176, and/or Y195, and a C' substitution sequence. In some such embodiments, the one or more substitutions is R158A, K176E, and/or Y195N.

Also provided are proteins that comprise one or more substitutions that renders the fluorescent protein pH stable, i.e. it has a pKa from about 2 to 6.5, usually from about 3 to 6 and more usually from about 3.5 to 6. pH titrations are performed by using a series of buffers in the pH range from 3 to 10. For each pH value, an aliquot of purified protein is diluted in an equal volume of the corresponding buffer solution and the fluorescence brightness is measured after 1 h incubation at room temperature. For accuracy, the actual pH is measured in each sample using a microelectrode (Sartorius). In some embodiments, the substitution is at the position corresponding to 144 or 159 of SEQ ID NO:2. In some embodiments, the substitution is S144C, S144V, S144T, S144F, S144H, A159C, A159M, A159N, and/or A159V.

Also provided are proteins that comprise one or more substitutions that shifts the fluorescence of the protein in to the far-red spectrum, i.e. it has an absorbance maximum ranging from about 580 nm to 700 nm, usually from about 580 nm to 650 nm and more usually from about 580 to 630 nm, and often from about 580 to 620 nm, while the maximum of emission spectra of the subject proteins typically ranges from about 640 nm to 750 nm, usually from about 640 nm to 710 nm and more usually from about 640 to 690 nm while in many embodiments the maximum of emission spectra ranges from about 640 to 680 nm. In some embodiments, the substitution is at a position corresponding to L14, M42, Q107, R198 or E216 of SEQ ID NO:2. In some embodiments, the substitution is L14V, L14E, M42L, M42V, M42A, M42T, M42S, M42C, M42N, Q107E, Q107D, Q107N, Q107V, R198Y, R198E, R198G, and/or E216Q.

Additional aspects of the invention include proteins which comprise one or more substitutions that makes the protein fluoresce orange, i.e. it has an absorbance maximum ranging from about 530 nm to 580 nm, usually from about 530 nm to 570 nm and more usually from about 540 to 560 nm, and often from about 545 to 560 nm, while the maximum of emission spectra of the subject proteins typically ranges from about 540 nm to 630 nm, usually from about 550 nm to 610 nm and more usually from about 560 to 600 nm while in many embodiments the maximum of emission spectra ranges from about 570 to 590 nm. In some embodiments, the substitution is at position corresponding to K68, S144, A159, L175, or R198 of SEQ ID NO:2. In some embodiments, the substitution is K68R, S144C, S144V, S144T, S144N, S144F, S144I, A159S, A159T, A159G, L175F, L175Y, L175M, R198H, R198S, and/or R198T.

Also provided are proteins which comprise one or more substitutions that makes the protein fluoresce blue, i.e. it has an absorbance maximum ranging from about 340 nm to 450 nm, usually from about 360 nm to 430 nm and more usually from about 380 to 420 nm, and often from about 390 to 410 nm, while the maximum of emission spectra of the subject proteins typically ranges from about 400 nm to 490 nm, usually from about 420 nm to 470 nm and more usually from about 430 to 470 nm while in many embodiments the maximum of emission spectra ranges from about 440 to 460 nm. In some embodiments, the blue substitution is a substitution at a position corresponding to M64, S144, A159, or R198 of SEQ ID NO:2. In some embodiments, the substitution that converts the protein to a blue fluorescent protein is M64I, M64Y, M64L, S144F, S144H, S144Y, S144L, A159N, A159D, A159Q, R198Y, and/or R198H.

Also provided are proteins which comprise one or more dual-color substitutions, that is, a substitution that makes the protein have two fluorescence excitation maxima and two fluorescent emission maxima. In some embodiments, absorbance maxima range from about 460 nm to 510 nm and from about 560 nm to 610 nm, while the maxima of emission spectra of the subject proteins range from about 500 nm to 540 nm and from about 570 nm to 650 nm. In some embodiments, the dual-color substitution is a substitution at a position corresponding to A159 of SEQ ID NO:2. In some embodiments, the substitution is A159C, A159N, A159D, A159Q, A159V, or A159T.

Additional aspects of the invention include proteins comprising one or more photostabilizing substitutions, that is, a substitution that makes the protein more photostable, i.e. it is photobleached slower than without this substitution. As used herein, "photostability" is stability of protein fluorescence upon light irradiation under excitation wavelength. As used herein, "photobleaching" means the photochemical destruction of a fluorophore (chromophore) of fluorescent protein. Photostability rate is defined as a relative photobleaching speed. Photostability and photobleaching are characterized by fluorescence intensity decrease in course of irradiation by light of excitation wavelength and certain intensity.

There are several methods known in the art to measure photobleaching and photostability. See, for example, methods described by Chiu et al. (J. Neurosci. Methods (2001), 105, 55-63), Wiedenmann et al. (Proc Natl Acad Sci USA. (2002) 99, 11646-11651), Rettig et al. (Springer-Verlag, 1999, p. 206-207) and Shaner et al. (Nat Biotechnol. (2004), 22(12):1567-1572; Nat Methods. 2005; 2(12):905-909), the disclosures of which are incorporated herein. For example, photostability may be compared in living cells transiently transfected with a mutant fluorescent protein. Wide-field and laser scanning confocal microscopy photobleaching comparisons are performed, and the half-time of fluorescence decay is compared for various proteins in identical conditions of irradiation. The fluorescence intensity of a cell is measured before and after bleaching by extensive irradiation with excitation light. After several rounds of sequential detection-bleaching (usually after 10-300 rounds, more usually after 20-200 rounds, and preferable after 30-100 rounds) bleaching curves are prepared using data obtained from detecting channel of the microscope and appropriate software. The half-time of fluorescence decay (i.e. irradiation duration needed to halve fluorescence intensity relative to the initial level) is then extrapolated from bleaching curves.

For example, a Leica AF6000 LX imaging system based on a DMI 6000 B inverted microscope can be used for photostability measurements of fluorescent proteins in host-cells with 63× immersion oil objective (effective magnification ratio 630×). GFP filter cube can be used for green fluorescent proteins and TX2 filter cube can be used for red fluorescent proteins. The field of view (containing several fluorescent cells) is selected and irradiated with appropriate filter set in series of detecting (e.g., intensity 1, gain 1, exposure length 10-100 ms) and bleaching (e.g. intensity 5, gain 1, exposure length 5 s) exposures. After 30-100 frames of detection/bleaching, one can draw the bleaching curves using data from detecting channel and appropriate software. Bleaching curves are normalized and compared. Longer photobleaching half-time means higher photostability.

Detecting light allows one to measure the fluorescence signal value. It is a relatively low intensity light of fluorescence excitation wavelength. An intensity of detecting light should be calibrated with the output signal value in such a way as to fit this value into the dynamic range of CCD detector used. In each particular case detecting light intensity depends on the initial fluorescence brightness, microscope, detector and excitation light source type. Also detecting light does not considerably bleach the fluorescence (or its bleaching ability is as low as possible).

As used herein, "bleaching light" means a relatively high intensity (for example 1 W/cm2) light of fluorescence excitation wavelength. Its intensity may be chosen as a maximum available with a particular microscope. Output signal usually doesn't matter and is not acquired for the further calculations. Bleaching light should provide the effective bleaching of fluorescence (bleaching is controlled by the detecting channel data respectively). In some cases, one can use bleaching light for both fluorescent protein bleaching and fluorescence signal measurement.

In some embodiments, the one or more photostabilizing mutations is one or more substitutions at positions corresponding to F63, M64, S144, A159, and/or R198 of SEQ ID NO:2. In some embodiments, the substitution is F63C, F63I, M64C, M64Y, M64T, M64Q, M64S, M64L, S144C, S144V, S144N, S144F, S144H, A159C, A159M, A159N, A159V, R198E, or R198I.

Additional aspects of the invention include proteins comprising a mutation that provides for a rapid rate of folding and maturation upon expression in the host cell. By rapidly folding and maturing rate it is meant that the protein achieves a tertiary structure that gives rise to its fluorescent quality in a short period of time. In these embodiments, the proteins folds and matures with a half-life that generally does not exceed about 48 hours, usually does not exceed about 12 hours and more usually does not exceed about 3 hours. To measure the maturation rate, transformed E. coli cells (XL1 Blue strain) expressing appropriate mutant protein may be grown overnight in LB supplemented with ampicillin and 2% D-glucose.

Tubes are filled to the rim and sealed upon induction to restrict oxygen availability. The bacterial cultures are centrifuged and the cell pellets re-suspended in 20 mM Tris-HCl, 100 mM NaCl, pH 7.5 buffer and lysed by sonication. The recombinant proteins are purified using TALON metal-affinity resin (Clontech). Maturation is performed at 37° C., in 35 mM KCl, 2 mM $MgCl_2$, 50 mM Tris pH 7.5, 1 mM DTT. A Varian Cary Eclipse Fluorescence Spectrophotometer or spectrophotometer SMS 2 VIS built into the stereomicroscope Olympus SZX-12 can be used for measuring maturation kinetics by monitoring growth of fluorescent signal. In some embodiments, the mutation that provides for a rapid rate of folding and maturation is a substitution at a position corresponding to H11, A46, N72, T74, Q75, I122, S129, T147, L148, K186, K208 of SEQ ID NO:2. In some embodiments, the substitution is H11P, A46V, A46G, A46S, N72K, T74P, T74G, T74S, I122V, I122A, S129A, T147G, T147S, L148M, K186T, K208N, K208S, K208G, or K208D.

Additional aspects of the invention include proteins comprising a mutation that provides for reversible photoactivation, i.e. the protein is capable of pronounced (at least 2-fold) and reversible changes in fluorescence brightness in response to irradiation of light of particular wavelength. Phenomenon of photoactivation and its reversibility can be observed in any fluorescent microscope equipped with laser or arc lamp light source. Irradiation at particular wavelength leads to pronounced (at least 2-fold) changes in fluorescence brightness. For the reversibly photoactivatable fluorescent protein, the initial fluorescent signal restores (at least to 50%-100%) after several minutes but no longer than 1 hour, and/or can be restored by irradiation using light of another wavelength.

In some embodiments, the wavelength of irradiating light required for the photoactivation ranges from about 420 nm to 480 nm (blue light). In some embodiments, the wavelength of required irradiating light ranges from about 480 nm to 570 nm (green light). In some embodiments, the mutation that provides for reversible photoactivation is a substitution at the position corresponding to S144, A159 or R198 of SEQ ID NO:2. In some embodiments, the substitution is S144C, S144G, S144T, S144H, A159C, A159G, A159S, A159C, R198Y, R198H.

Mutants and derivates can be generated using standard techniques of molecular biology as described in details in the section "Nucleic acid molecules" above. Several mutants are described herein. Given the guidance provided in the Examples, and using standard techniques, those skilled in the art can readily generate a wide variety of additional mutants and test whether a biological (e.g. biochemical, spectral, etc.) property has been altered. For example, mutations that reduce oligomerization of a fluorescent protein can be combined with mutations that improve protein folding and/or alter protein photostability, excitation/emission spectra and/or pH-stability, capability of photoactivation, etc.

For screening of mutant variants, nucleic acids encoding these variants are cloned into suitable expression vector (for example pQE30 vector, Qiagen) and expressed in host cells (for example in E. coli XL1 Blue strain, Invitrogen). Depending on the complexity of library, from 100 to 100,000 individual clones each expressing individual FP variant are screened using a fluorescent stereomicroscope equipped with the appropriate filter set (excitation filter 545-580 nm, emission filter 610LP). Fluorescence intensity can be also measured using a spectrophotometer at various excitation wavelengths.

The proteins of the subject invention are separated from their naturally-occurring environment. For example, purified protein is provided, where "purified" means that the protein is present in a mixture that is substantially free of non-chromogenic or fluorescent proteins of interest, where "substantially free" means that less than 90%, usually less than 60% and more usually less than 50% of the mixture content is non-chromogenic or fluorescent proteins or mutants thereof. The proteins of the present invention also may be present in the isolated form, by which is meant that the protein is substantially free of other proteins and other naturally-occurring biological molecules, such as oligosaccharides, nucleic acids and fragments thereof, and the like, where the term "substantially free" in this instance means that less than 70%, usually less than 60% and more usually less than 50% of the composition containing the isolated protein is some other natural occurring biological molecule. In some embodiments, the proteins are present in substantially purified form, where by "substantially purified form" means at least 95%, usually at least 97% and more usually at least 99% pure.

The subject proteins and polypeptides may be synthetically produced. For example, wild type proteins may be derived from biological sources which express the proteins. The subject proteins may be derived from synthetic means, e.g. by expressing a recombinant nucleic acid coding sequence encoding the protein of interest in a suitable host, as described above. Any convenient protein purification procedures may be employed, where suitable protein purification methodologies are described in Guide to Protein Purification, (Deuthser ed., Academic Press, 1990). For example, a lysate may be prepared from the original source and purified using HPLC, exclusion chromatography, gel electrophoresis, affinity chromatography, and the like.

Also provided are fusion proteins comprising a protein of the present invention, fused, for example, to a degradation sequence, a sequence of subcellular localization (e.g. nuclear localization signal, peroximal targeting signal, Golgi apparatus targeting sequence, mitochondrial targeting sequence, protein with known subcellular localization, etc.), a signal peptide, or any protein or polypeptide of interest. Fusion proteins may include for example, a fluorescent protein of the subject invention or mutant thereof and a second polypeptide ("the fusion partner") fused in-frame at the N-terminus and/or C-terminus of the fluorescent protein. Fusion partners include, but are not limited to, polypeptides that can bind antibodies specific to the fusion partner (e.g., epitope tags), antibodies or binding fragments thereof, polypeptides that provide a catalytic function or induce a cellular response, ligands or receptors or mimetics thereof, and the like. In such fusion proteins, the fusion partner is generally not naturally associated with the fluorescent protein portion of the fusion protein.

Fusion proteins can be produced using recombinant technologies well known in the art. To generate fusion proteins, a nucleic acid encoding a subject protein is operatively linked with the nucleic acid encoding "fusion partner". In the resulted nucleic acid coding sequence of the fluorescent protein and coding sequence of the "fusion partner" are covalently linked so that no frameshifts and stop codons are present between these coding sequences.

Also provided are antibodies that bind specifically to the subject fluorescent proteins and mutants thereof. Suitable antibodies may be produced using the techniques known in the art. For example, polyclonal antibodies may be obtained as described in (Harlow and Lane Antibodies: A Laboratory Manual, (1988) Cold Spring Harbor Laboratory Press, Cold Spring Harbor, N.Y.) and monoclonal antibodies may be obtained as described in (Goding Monoclonal Antibodies: Principles and Practice: Production and Application of Monoclonal Antibodies in Cell Biology, Biochemistry and Immunology; 3rd edition, (1996) Academic Press). Chimeric antibodies including humanized antibodies as well as single-chain antibodies and antibody fragments such as Fv, F(ab')2 and Fab are also of interest.

Transformants

The nucleic acids of the present invention can be used to generate transformants including transgenic organisms or site-specific gene modifications in cell lines. Transgenic cells of the subject invention include one or more nucleic acids according to the subject invention present as a transgene. For the purposes of the invention any suitable host cell may be used including prokaryotic (e.g. *Escherichia coli, Streptomyces* sp., *Bacillus subtilis, Lactobacillus acidophilus*, etc) or eukaryotic host-cells. Transgenic organism of the subject invention can be prokaryotic or a eukaryotic organism including bacteria, cyanobacteria, fungi, plants and animals, in which one or more of the cells of the organism contains heterologous nucleic acid of subject invention introduced by way of human intervention, such as by transgenic techniques well known in the art.

The isolated nucleic acid of the present invention can be introduced into the host by methods known in the art, for example infection, transfection, transformation or transconjugation. Techniques for transferring the nucleic acid molecules (i.e. DNA) into such organisms are widely known and provided in references such as Sambrook et al. (Molecular Cloning: A Laboratory Manual, 3nd Ed., (2001) Cold Spring Harbor Press, Cold Spring Harbor, N.Y.).

In one embodiment, the transgenic organism can be a prokaryotic organism. Methods on the transformation of prokaryotic hosts are well documented in the art (for example see Sambrook et al. Molecular Cloning: A Laboratory Manual, 2nd edition (1989) Cold Spring Harbor Laboratory Press and Ausubel et al., Current Protocols in Molecular Biology (1995) John Wiley & Sons, Inc).

In another embodiment, the transgenic organism can be a fungus, for example, yeast. Yeast is widely used as a vehicle for heterologous gene expression (for example see Goodey et al Yeast biotechnology, D R Berry et al, eds, (1987) Allen and Unwin, London, pp 401-429) and by King et al Molecular and Cell Biology of Yeasts, E F Walton and G T Yarronton, eds, Blackie, Glasgow (1989) pp 107-133). Several types of yeast vectors are available, including integrative vectors, which require recombination with the host genome for their maintenance, and autonomously replicating plasmid vectors.

Another host organism is an animal. Transgenic animals can be obtained by transgenic techniques well known in the art and provided in references such as Pinkert, Transgenic Animal Technology: a Laboratory Handbook, 2nd edition (2203) San Diego Academic Press; Gersenstein and Vintersten, Manipulating the Mouse Embryo: A Laboratory Manual, 3rd ed, (2002) Nagy A. (Ed), Cold Spring Harbor Laboratory; Blau et al., Laboratory Animal Medicine, 2nd Ed., (2002) Fox J. G., Anderson L. C., Loew F. M., Quimby F. W. (Eds), American Medical Association, American Psychological Association; Gene Targeting: A Practical Approach by Alexandra L. Joyner (Ed.) Oxford University Press; 2nd edition (2000). For example, transgenic animals can be obtained through homologous recombination, where the endogenous locus is altered. Alternatively, a nucleic acid construct is randomly integrated into the genome. Vectors for stable integration include plasmids, retroviruses and other animal viruses, YACs, and the like.

The nucleic acid can be introduced into the cell, directly or indirectly by introduction into a precursor of the cell, by way of deliberate genetic manipulation, such as by microinjection or by infection with a recombinant virus or with a recombinant viral vector and the like. The term genetic manipulation does not include classical cross-breeding, or in vitro fertilization, but rather is directed to the introduction of a recombinant nucleic acid molecule. This nucleic acid molecule may be integrated within a chromosome, or it may be extrachromosomally replicating DNA.

DNA constructs for homologous recombination will comprise at least a portion of a nucleic acid of the present invention, wherein the gene has the desired genetic modification(s), and includes regions of homology to the target locus. DNA constructs for random integration need not include regions of homology to mediate recombination. Conveniently, markers for positive and negative selection may be included. Methods for generating cells having targeted gene modifications through homologous recombination are known in the art. For various techniques for transfecting mammalian cells, see Keown et al., Meth. Enzymol. (1990) 185:527-537.

For embryonic stem (ES) cells, an ES cell line may be employed, or embryonic cells may be obtained freshly from a host, such as a mouse, rat, guinea pig, etc. Such cells are grown on an appropriate fibroblast-feeder layer or grown in the presence of leukemia inhibiting factor (LIF). Tansformed ES or embryonic cells may be used to produce transgenic animals using the appropriate technique described in the art.

The transgenic animals may be any non-human animals including non-human mammal (e.g. mouse, rat), a bird or an amphibian, etc., and used in functional studies, drug screening and the like. Representative examples of the use of transgenic animals include those described infra.

Transgenic plants also may be produced. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants also are reviewed in Plant Biochemistry and Molecular Biology (eds. Lea and Leegood, John Wiley & Sons, 1993, pp. 275-295) and in Plant Biotechnology and Transgenic Plants (eds. Oksman-Caldentey and Barz, 2002).

For example, embryogenic explants comprising somatic cells may be used for preparation of the transgenic host. Following cell or tissue harvesting, exogenous DNA of interest is introduced into the plant cells, where a variety of different techniques is available for such introduction. With isolated protoplasts, the opportunity arises for introduction via DNA-mediated gene transfer protocols, including incubation of the protoplasts with naked DNA, such as plasmids comprising the exogenous coding sequence of interest in the presence of polyvalent cations (for example, PEG or PLO); or electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, such as auxins and cytokinins.

Other suitable methods for producing plants may be used such as "gene-gun" approach or *Agrobacterium*-mediated transformation available for those skilled in the art.

Methods of Use

The fluorescent proteins of the present invention (as well as other components of the subject invention described herein) find use in a variety of different applications. For example, they may be used in the methods for labeling, analyzing or detecting a biological molecule, cell or cell organelle. Representative uses for each of these types of proteins will be described below, where the uses described herein are merely exemplary and are in no way meant to limit the use of the proteins of the present invention to those described.

The subject proteins find use in methods for monitoring pH in a cell or cell compartment. Those proteins of the subject invention that are pH sensitive they can be used to detect pH change within physiological range. The method is particularly suitable for measuring pH in a specific region of the cell, e.g., the cytosol, or an organellar space such as the inner mitochondrial matrix, the lumen of the Golgi, cytosol, the endoplasmic reticulum, the chloroplast lumen, the lumen of lysosome, or the lumen of an endosome. The method comprises expression of the subject protein in a cell alone or in fusion with specific subcellular localization signal that target the protein to desired cell compartment. pH change around the fluorescent protein results in change of spectral characteristic of the protein that can be measured.

In another embodiment relating to the method for labeling a biological molecule, cell or cell organelle, the subject proteins find use as labels (or reporter molecules) in cell and molecular biology assays. The assays of interest include but not limited to assays for gene expression, protein localization and co-localization, protein-protein interactions, protein-nucleic acid interactions, nucleic acid-nucleic acid interactions, cell and cell organelle localization and interactions, etc. The fluorescent proteins of the present invention find use as a biomolecule labels, or cell organelle labels in living and fixed cells; as a markers in cell or organelle fusion, as a cell or organelle integrity markers, as a transfection markers (e.g. as labels for selection of transfected cells containing an expression vector encoding at least one fluorescent protein of the invention), as real-time probe working at near physiological concentrations, etc.

In particular, the subject proteins find use for identifying and/or measuring the expression of protein or polypeptide of interest in the biological material (e.g. host cells). This method comprises: i) introducing into a cell a nucleic acid molecule comprising a nucleotide sequence encoding a fluorescent protein according to the present invention wherein the nucleic acid molecule is operably linked to and under the control of an expression control sequence which moderates expression of the protein or polypeptide of interest; ii) culturing the cell under conditions suitable for the expression of the protein of interest; and iii) detecting the fluorescence emission of the fluorescent protein as a means of measuring the expression/localization of the protein of interest.

In particular, the subject proteins find use for identifying and/or localization of protein or polypeptide of interest in biological material. This method comprises: i) introducing into a cell a nucleic acid molecule comprising a nucleotide sequence encoding a fluorescent protein according to the present invention wherein the nucleic acid molecule is operably linked with sequence encoding protein or polypeptide of interest and under the control of an promoter sequence; ii) culturing the cell under conditions suitable for the expression of the protein of interest; and iii) detecting the fluorescence emission of the fluorescent protein as a means of measuring the expression/localization of the protein of interest.

The term "operatively linked" or "operably linked" or the like, when used to describe chimeric proteins, refer to polypeptide sequences that are placed in a physical and functional relationship to each other. In a most preferred embodiment, the functions of the polypeptide components of the chimeric molecule are unchanged compared to the functional activities of the parts in isolation. For example, a fluorescent protein of the present invention can be fused to a fusion partner of interest. In this case, the fusion molecule retains its fluorescence, and the polypeptide of interest retains its original biological activity. In some embodiments of the present invention, the activities of either the fluorescent protein or the protein of interest can be reduced relative to their activities in isolation. Such fusions can also find use with the present invention.

The term "operably linked" as used herein when used to describe nucleic acid molecules and regulatory sequences refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that the reading frame is maintained and a functional protein is produced.

The applications of interest include the use of the subject proteins in fluorescence resonance energy transfer (FRET) methods. In these methods, the subject proteins serve as donor and/or acceptors in combination with a second fluorescent protein or dye, for example, a fluorescent protein as described in Matz et al., Nature Biotechnology 17:969-973 (1999); a mutants of green fluorescent protein from *Aequorea victoria*, for example, as described in U.S. Pat. No. 6,066,476; U.S. Pat. No. 6,020,192; U.S. Pat. No. 5,985,577; U.S. Pat. No. 5,976,796; U.S. Pat. No. 5,968,750; U.S. Pat. No. 5,968,738; U.S. Pat. No. 5,958,713; U.S. Pat. No. 5,919,445; U.S. Pat. No. 5,874,304, the disclosures of which are herein incorporated by reference; other fluorescent dyes such as coumarin and its derivatives, 7-amino-4-methylcoumarin and aminocoumarin; bodipy dyes; cascade blue; or fluorescein and its derivatives, such as fluorescein isothiocyanate and Oregon green; rhodamine dyes such as Texas red, tetramethylrhodamine, eosins and erythrosins; cyanine dyes such as Cy3 and Cy5; macrocyclic chealates of lenthaninde ions, such as quantum dye; and chemilumescent dyes such as luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference.

Specific examples of where FRET assays employing the subject fluorescent proteins may be used include, but are not limited to, the detection of protein-protein interactions, such as in a mammalian two-hybrid system, transcription factor dimerization, membrane protein multimerization, multiprotein complex formation; as a biosensor for a number of different events, where a peptide or protein covalently links a FRET fluorescent combination including the subject fluorescent proteins and the linking peptide or protein is, for example, a protease-specific substrate for caspase-mediated cleavage, a peptide that undergoes conformational change upon receiving a signal which increases or decreases FRET, such as a PKA regulatory domain (cAMP-sensor), a phosphorylation site (for example, where there is a phosphorylation site in the peptide or the peptide has binding specificity to phosphorylated/dephosphorylated domain of another protein), or the peptide has Ca2+ binding domain. In addition, fluorescence resonance energy transfer or FRET applications in which the proteins of the present invention find use include, but are not limited to, those described in: U.S. Pat. Nos. 6,008,373; 5,998,146; 5,981,200; 5,945,526; 5,945,283; 5,911,952; 5,869,255; 5,866,336; 5,863,727; 5,728,528; 5,707,804; 5,688,648; 5,439,797; the disclosures of which are herein incorporated by reference.

The fluorescent proteins of the present invention find use in a method for detecting the effects of a test substance on the regulation of expression and/or translocation of one or more proteins of interest in a cell. Alternatively, they find use in a method for detecting the expression of a protein of interest and the simultaneous activity of an expression control sequence in response to a test substance. The fluorescent proteins find also use in a method to compare the activity of two or more expression control sequences in a cell in response to a test substance. Such methods may be performed in the presence and in the absence of a test substance whose effect on the process is to be measured.

The fluorescent proteins of the present invention also find use in applications involving the automated screening of arrays of cells expressing fluorescent reporting groups by using microscopic imaging and electronic analysis. Screening can be used for drug discovery and in the field of functional genomics where the subject proteins are used as markers of whole cells to detect changes in multicellular reorganization and migration, for example in the formation of multicellular tubules (blood vessel formation) by endothelial cells, migration of cells through the Fluoroblok Insert system (Becton Dickinson Co.), wound healing, or neurite outgrowth. Screening can also be employed where the proteins of the present invention are used as markers fused to peptides (such as targeting sequences) or proteins that detect changes in intracellular location as an indicator for cellular activity, for example in signal transduction, such as kinase and transcription factor translocation upon stimuli. Examples include protein kinase C, protein kinase A, transcription factor NFkB, and NFAT; cell cycle proteins, such as cyclin A, cyclin B1 and cyclin E; protease cleavage with subsequent movement of cleaved substrate; phospholipids, with markers for intracellular structures such as the endoplasmic reticulum, Golgi apparatus, mitochondria, peroxisomes, nucleus, nucleoli, plasma membrane, histones, endosomes, lysosomes, or microtubules.

The proteins of the present invention also can be used in high content screening to detect co-localization of other fluorescent fusion proteins with localization markers as indicators of movements of intracellular fluorescent proteins/peptides or as markers alone. Examples of applications involving the automated screening of arrays of cells in which the subject fluorescent proteins find use include U.S. Pat. No. 5,989,835; as well as WO 0017624; WO 00/26408; WO 00/17643; and WO 00/03246; the disclosures of which are herein incorporated by reference.

The fluorescent proteins of the present invention also find use in high throuphput screening assays. The subject fluorescent proteins are stable proteins with half-lives of more than 24 hours. Also provided are destabilized versions of the subject fluorescent proteins with decreased half-lives that can be used as transcription reporters for drug discovery. For example, a protein according to the subject invention can be fused with a putative proteolytic signal sequence derived from a protein with shorter half-life, such as a PEST sequence from the mouse ornithine decarboxylase gene, a mouse cyclin B1 destruction box or ubiquitin, etc. For a description of destabilized proteins and vectors that can be employed to produce the same, see e.g., U.S. Pat. No. 6,130,313; the disclosure of which is herein incorporated by reference. Promoters in signal transduction pathways can be detected using destabilized versions of the subject fluorescent proteins for drug screening such as, for example, AP1, NFAT, NFkB, Smad, STAT, p53, E2F, Rb, myc, CRE, ER, GR and TRE, and the like.

The subject proteins can be used as second messenger detectors by fusing the subject proteins to specific domains such as the PKCgamma Ca binding domain, PKCgamma DAG binding domain, SH2 domain or SH3 domain, etc.

Secreted forms of the subject proteins, which in turn can be used in a variety of different applications can be prepared by fusing secreted leading sequences to the subject proteins.

The subject proteins also find use in fluorescence activated cell sorting (FACS) applications. In such applications, the subject fluorescent protein is used as a label to mark a population of cells and the resulting labeled population of cells is then sorted with a fluorescent activated cell sorting device, as is known in the art. FACS methods are described in U.S. Pat. Nos. 5,968,738 and 5,804,387; the disclosures of which are herein incorporated by reference.

The subject proteins also find use as in vivo labels in transgenic animals. For example, expression of the subject protein can be driven by tissue-specific promoters, where such methods find use in research for gene therapy, such as testing efficiency of transgenic expression, among other applications. A representative application of fluorescent proteins in transgenic animals that illustrates such applications is found in WO 00/02997, the disclosure of which is herein incorporated by reference.

Additional applications of the proteins of the present invention include use as markers following injection into cells or animals and in calibration for quantitative measurements; as markers or reporters in oxygen biosensor devices for monitoring cell viability; as markers or labels for animals, pets, toys, food, and the like.

The subject fluorescent proteins also find use in protease cleavage assays. For example, cleavage-inactivated fluorescence assays can be developed using the subject proteins, where the subject proteins are engineered to include a protease-specific cleavage sequence without destroying the fluorescent character of the protein. Upon cleavage of the fluorescent protein by an activated protease, fluorescence would sharply decrease due to the destruction of the functional chromophore. Alternatively, cleavage-activated fluorescence can be developed using the proteins of the present invention where the proteins are engineered to contain an additional spacer sequence in close proximity/or inside the chromophore. This variant is significantly decreased in its fluorescent activity, because parts of the functional chromophore are divided by the spacer. The spacer is framed by two identical protease-specific cleavage sites. Upon cleavage via the activated protease, the spacer would be cut out and the two residual "subunits" of the fluorescent protein would be able to reassemble to generate a functional fluorescent protein. Both of the above applications could be developed in assays for a variety of different types of proteases, such as caspases and others.

The subject proteins also can be used in assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes, while allowing co-localization of membrane proteins in specific phospholipid rafts, can be accomplished with the subject proteins.

The subject fluorescent proteins also find use as biosensors in prokaryotic and eukaryotic cells, such as a $Ca^{2+}$ ion indicator; a pH indicator; a phosphorylation indicator; or as an indicator of other ions, such as magnesium, sodium, potassium, chloride and halides. Methods of using fluorescent proteins as biosensors also include those described in U.S. Pat. Nos. 5,972,638; 5,824,485 and 5,650,135 (as well as the references cited therein) the disclosures of which are herein incorporated by reference.

The antibodies of the subject invention, described above, also find use in a number of applications, including the differentiation of the subject proteins from other fluorescent proteins.

Kits

Also provided by the present invention are kits for use in practicing one or more of the above-described applications. Kits typically include the protein of the invention as such, or a nucleic acid encoding the same preferably with the elements for expressing the subject proteins, for example, a construct such as a vector comprising a nucleic acid encoding the subject protein. In preferred embodiments kits may be used for monitoring pH within living cells, subcellular structures or protein around. In other embodiments kits may be used for labeling of cells, subcellular structures or proteins.

The kit components are typically present in a suitable storage medium, such as a buffered solution, typically in a suitable container. Also present in the kits may be antibodies specific to the provided protein. In certain embodiments, the kit comprises a plurality of different vectors each encoding the subject protein, where the vectors are designed for expression in different environments and/or under different conditions, for example, constitutive expression where the vector includes a strong promoter for expression in mammalian cells or a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit.

The following example is offered by way of illustration and not by way of limitation.

EXAMPLES

Site directed mutagenesis and C-terminus replacement were performed by overlap-extension PCR (Ho, et al., 1989; Gene 77, 51-59), with primers containing the appropriate target substitutions. Clontech Diversity PCR Random Mutagenesis kit was used for random mutagenesis, in conditions optimal for 7 mutations per 1000 bp. For bacterial expression, a PCR-amplified BamHI/HindIII fragment encoding a fluorescent protein variant was cloned into the pQE30 vector (Qiagen). For expression in eukaryotic cells, a PCR-amplified AgeI/NotI fragment encoding a fluorescent protein variant was swapped for TurboGFP within the pTurboGFP-N vector (Evrogen).

Example 1

Generation of mKate2-Based Monomerized pH-Sensitive Fluorescent Proteins

A nucleic acid (SEQ ID NO:1) encoding mKate2 protein (SEQ ID NO:2) was obtained from commercially available vector pmKate2-C (Evrogen, Moscow, Russia). Site directed mutagenesis was performed to obtain mKate2 variants comprising a 176E substitution and\or a 159S substitution. Variants obtained were transformed in E. coli (XL1-blue strain). E. coli colonies expressing mutant proteins were grown at 37° C. and recombinant proteins were purified via a metal-affinity resin TALON (Clontech). Purified proteins were tested using FPLC for oligomeric status, excitation-emission spectra were obtained using Varian Cary Eclipse Fluorescence Spectrophotometer under various pH. A 176E substitution resulted in a reduction in the dimerization capacity of mKate2 according to FPLC data, while a 159S substitution resulted in an increased sensitivity of the chromophore to pH. A random mutation at K136R was generated in the course of generating these mutations. The reverse mutant, i.e. a lysine (K) at residue 136 as in wild type mKate2, had substantially the same properties as variants with the arginine (R) at this residue.

A variant comprising both substitutions 176E and 159S as well as amino acid substitutions A46V, K136R, and T147M was also produced (pH-Redder-0.1 variant, SEQ ID NO:5, SEQ ID NO:6). It has a pKa=7.3 and suitable pH-stability curve for monitoring of pH changes in physiological range (from pH 5.5 to pH 8.0).

Example 2

Generation of the Essentially Monomerized Fluorescent Protein on the Basis of mKate2

Mutant variants of mKate2 with an essentially reduced tendency to form dimers were designed based on the structure of mKate at pH7.5 (PDB ID: 3BXB). Both mKate and mKate2 behave as monomers in gel filtration (size exclusion chromatography) performed using low pressure liquid chromatography (LPLC). However, the crystal form corresponds to the much higher protein concentration, where mKate adopts tetrameric arrangement, typical for the Anthozoa GFP-like proteins. The interacting surfaces of the subunits form two interfaces. While interface 1 (hydrophobic) is rather weak, interface 2 (hydrophilic) is much stronger, and is additionally stabilized by the C-terminal tail of the protein, consisting of residues 223-232. This C-terminal tail extends away from the β-barrel, interacting instead with the cylindrical surface of the interacting counterpart contributing to the interface 2.

Based on this structure and on the previous studies of interfaces of GFP-like protein tetramers, we selected amino acid residues R158, K176, and Y195 of the second interface as well as residues in the C terminus of mKate2 (positions 223-232 and in particular L225) as key positions that could be changed in order to further destabilize protein dimerization.

A nucleic acid (SEQ ID NO:1) encoding mKate2 protein was obtained as described in the Example 1. Site directed mutagenesis was performed to obtain mKate2 variants comprising the amino acid substitutions R158A, R158S, R158D, R158N, R158G, K176E, K176N, K176D, K176S; Y195N, Y195D, Y195V, Y195A, Y195T, Y195E, Y195S, Y195C, Y195G; L225G, L225E, L225A, L225T, L225N, or L225G, or a substitution of the C terminal 10 amino acids with a substitution C terminus of STGGAGDGGK (SEQ ID NO:31). Resulting mutant variants were transformed in E. coli (XL1-blue strain). E. coli colonies expressing mutant protein were grown at 37° C. and recombinant proteins were purified via a metal-affinity resin TALON (Clontech). Purified proteins were tested using FPLC for oligomeric status, excitation-emission spectra were obtained using spectrophotometer SMS 2 VIS built into the Olympus SZX-12 stereomicroscope under various pH.

After introducing substitutions to all or some of these positions, the monomeric nature of resulting proteins were verified using FPLC at concentration 1 mg/ml or higher. These substitutions reduced the oligomerization of the fluorescent proteins, as characterized by a decreased tendency to form dimers according to FPLC data. However, some variants exhibited a considerably dimmer fluorescence as compared to mKate2, e.g. variants comprising substitutions in three residues (R158, K176, Y195).

To rescue fluorescence brightness of the variants comprising three substitutions, saturated site-directed mutagenesis (all 20 amino acid variants) of the variant comprising R158A, K176E, and Y195N and a substituted C terminus was performed at the residue 159. Resulting mutants were screened to identify the brightest, pH-sensitive and pH-stable variants.

To select the brightest variants, mutants were screened by fluorescent stereomicroscopy with Olympus SZX-12 equipped with the appropriate filter set (excitation filter 545-580 nm, emission filter 610LP). The brightest variant, mKate2M1 (SEQ ID NO:3, SEQ ID NO:4), contained amino acid substitutions R158A, A159C, K176E, Y195N and a substituted C terminus.

To select pH-sensitive variants, excitation-emission spectra for the purified proteins were obtained using spectrophotometer SMS 2 VIS under various pH. pH sensitive variants identified included mKate2M1pHsens1 (SEQ ID NO:7, SEQ ID NO:8) contained Gly (G) at position 159. Two pH stable variants were also identified, namely mKate2M1stab1 (SEQ ID NO:13, SEQ ID NO:14) and mKate2M1stab2 (SEQ ID NO:15, SEQ ID NO:16), contained substitutions 159V and 159N, respectively. Both mKate2M1stab1 and mKate2M1stab2 demonstrated higher photostability compared to mKate2M1.

Example 3

Optimization of mKate2M1 Folding and Maturation

A nucleic acid encoding mKate2M1 protein was subjected to random mutagenesis. The resulting library of mutant variants was transformed in E. coli (XL1-blue strain). Approximately 100,000 E. coli colonies expressing mutant protein variants were grown at 37° C. overnight and screened for the brightest red fluorescent variants. The 50 brightest variants were sequenced. Those mutant variants that contained interface substitution potentially leading to dimerization were discarded. For example, enhanced variants characterized by brighter fluorescence and faster maturation often contained interface substitutions that could enhance dimerization, such as R123I (reverts to the wild type Ile123 of eqFP578 stabilizing the $1^{st}$ interface), E156V, A158V, D160V, E176V, E176F, and N195I (introduce hydrophobic residues in the $2^{nd}$ interface).

Other amino acid substitutions found in enhanced variants were T74P and K208N. These mutations were further united yielding a protein named mKate2M1fold1 (SEQ ID NO:9, SEQ ID NO:10), which demonstrated enhanced brightness relative to mKate2M1 after overnight expression at 37° C., indicating faster folding and maturation at 37° C.

mKate2M1fold1 (SEQ ID NO:9, SEQ ID NO:10) was then subjected to saturated site-directed mutagenesis (all 20 amino acid variants) at amino acid positions 74 and 208. The resulting library of mutant variants was transformed in E. coli (XL1-blue strain). Approximately 10,000 E. coli colonies expressing mutant protein variants were grown at 37° C. overnight and screened for the brightest red fluorescent variants. An enhanced variant was selected, named mKate2M1fold2 (SEQ ID NO:11, SEQ ID NO:12) comprising 74G and 208S substitutions. This variant demonstrates enhanced brightness after overnight expression at 37° C. compared to mKate2M1fold1, indicating faster folding and maturation at 37° C.

Figure 3:
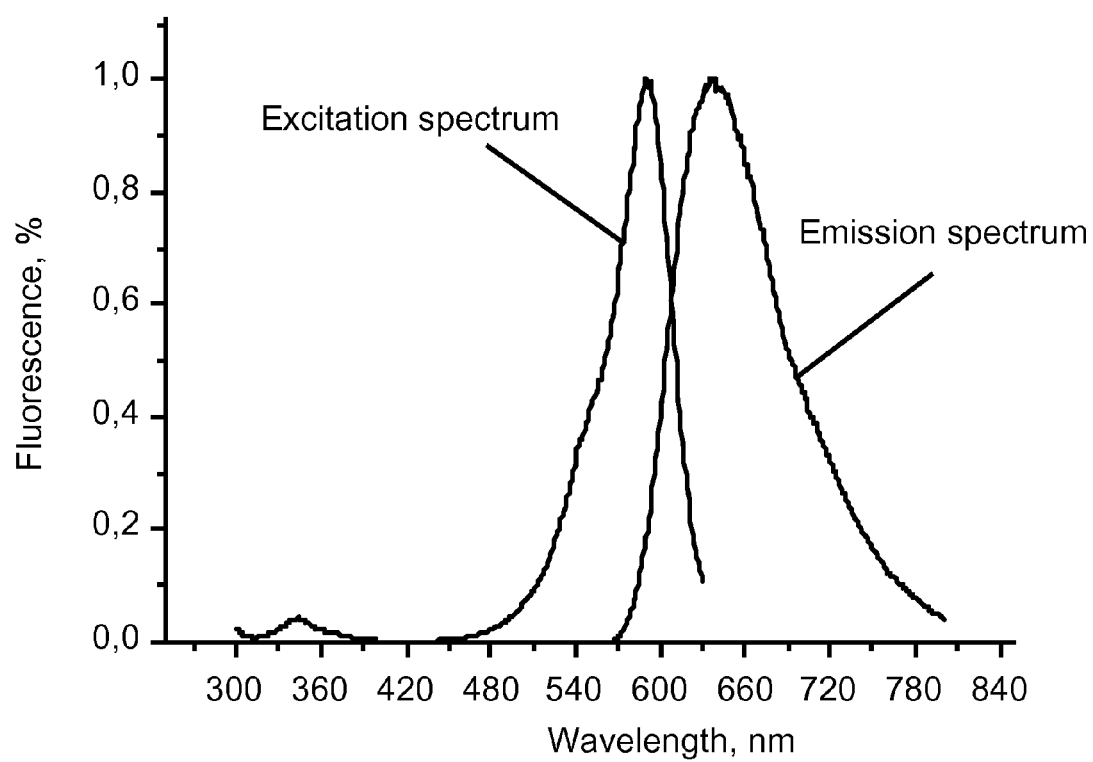
FIG. 3 illustrates normalized excitation and emission spectra of the mKate2.5 fluorescent protein.

In another experiment, mKate2M1fold1 (SEQ ID NO:9, SEQ ID NO:10) was subjected to random mutagenesis. The resulting library of mutant variants was transformed in E. coli (XL1-blue strain). Approximately 100,000 E. coli colonies expressing mutant protein variants were grown at 37° C. overnight and screened for the brightest red fluorescent variants. The 50 brightest variants were sequenced. Those mutant variants that contained interface substitution potentially leading to dimerization were discarded. The enhanced variant was selected, named mKate2.5 (SEQ ID NO:27, SEQ ID NO:28) comprising A46V and S129A substitutions. This variant also demonstrates enhanced brightness after overnight expression at 37° C. compared to mKate2M1fold1, indicating faster folding and maturation at 37° C. Excitation and emission spectra of the mKate2.5 are shown in FIG. 3.

Example 4

Generation of a Far-Red Shifted Fluorescent Protein on the Basis of mKate2M1

A nucleic acid encoding mKate2M1 protein was subjected to random mutagenesis. Resulting library of mutant variants was transformed in E. coli (XL1-blue strain). Approximately 100,000 E. coli colonies expressing mutant protein variants were grown at 37° C. overnight and screened for the far-red shifted fluorescent variants using fluorescent stereomicroscope equipped with appropriate filter sets and built-in fluorescent spectrophotometer. A far-red shifted mutant variant was selected and named mKate2M1farred1 (SEQ ID NO:17, SEQ ID NO:18). mKate2M1farred1 contains amino acid substitution M42L compared to mKate2M1, and demonstrates far-red shifted fluorescence emission compared with mKate2M1.

Example 5

Generation of Enhanced Far-Red Shifted Fluorescent Protein on the Basis of mKate2M1farred1

A nucleic acid encoding mKate2M1farred1 protein was subjected to saturated site-directed mutagenesis (all 20 amino acid variants) at amino acid position 42. Resulting library of mutant variants was transformed in E. coli (XL1-blue strain). Approximately 1,000 E. coli colonies expressing mutant protein variants were grown at 37° C. overnight and screened for the brightest far-red fluorescent variants. The brightest mutant variants that contained no casual interface substitutions potentially leading to dimerization was selected and named mKate2M1farred2 (SEQ ID NO:19, SEQ ID NO:20). mKate2M1farred2 contains a valine at 42 instead of a leucine, as in mKate2M1farred1, and demonstrates enhanced brightness after overnight expression at 37° C. compared to mKate2M1farred1, indicating faster maturation. mKate2M1farred2 still demonstrates far-red shifted fluorescence emission peaked at approximately 650 nm. A third far-red variant was also identified, mKate2M1farred3 (SEQ ID NO:21, SEQ ID NO:22), which contains the amino acid substitution 42V and an amino acid substitution 107N.

Example 6

Generation of an Orange-Shifted Fluorescent Protein on the Basis of mKate2M1

A nucleic acid encoding mKate2M1 protein was subjected to site-directed mutagenesis to substitute S144C, C159T, and R198Y, to generate an orange fluorescent protein analogous to the TagRFP. The resulting mutant variant was transformed in E. coli (XL1-blue strain). E. coli colony expressing mutant protein was grown at 37° C. and recombinant protein was purified via a metal-affinity resin TALON (Clontech). Excitation-emission spectra for the purified proteins were obtained using Varian Cary Eclipse Fluorescence Spectrophotometer. The resulting mutant, named mKate2M1orange1 (SEQ ID NO:23, SEQ ID NO:24) is characterized by orange-red fluorescence with fluorescence excitation peaked at approximately 560 nm and fluorescence emission peaked at approximately 580 nm.

Example 7

Generation of a Photoactivatable Red Fluorescent Protein on the Basis of mKate2M1

A nucleic acid encoding mKate2M1 protein was subjected to saturated site-directed mutagenesis (all 20 amino acid variants) at amino acid positions 144, 159, and site-directed mutagenesis R198H. Resulting library of mutant variants was transformed in *E. coli* (XL1-blue strain). Approximately 10,000 *E. coli* colonies expressing mutant protein variants were grown at 37° C. overnight and screened for the reversible photoconversion property in the fluorescent stereomicroscope. The photoactivatable protein named mKate2M1photo1 was selected (SEQ ID NO:25, SEQ ID NO:26). mKate2M1photo1 contains substitutions S144H and R198H as compared to mKate2M1. It is a bright red fluorescent protein that converts to a low fluorescent (10-fold fluorescence decrease) state upon green (545-580 nm) light irradiation and reverts to the bright red fluorescent state in response to blue (460-490 nm) light irradiation.

Example 8

Optimization of mKate2.5 Folding, Brightness and pH-Stability

A nucleic acid encoding mKate2.5 protein was obtained as described in the Example 3 and subjected to site-directed mutagenesis to substitute K68R and R198H. These mutations convert the chromophore environment to that of the wild type protein eqFP578 from *Entacmaea quadricolor*, which is characterized by high pH stability. The obtained mutant variant mKate2.6 (SEQ ID NOs:38, 39) showed increased pH stability.

This mutant was then subjected to random mutagenesis to enhance folding and maturation. The resulting library of mutant variants was transformed in *E. coli* (XL1-blue strain). Approximately 100,000 *E. coli* colonies expressing mutant protein variants were grown at 37° C. overnight and screened for the brightest red fluorescent variants. 50 brightest variants were sequenced. Those mutant variants that contained interface substitutions potentially leading to dimerization were discarded. From these experiments, the following substitutions were found that further enhanced folding and maturation: H11P, N72K, Q75P, I122V, L148M, K186T, N208D.

Figure 4:
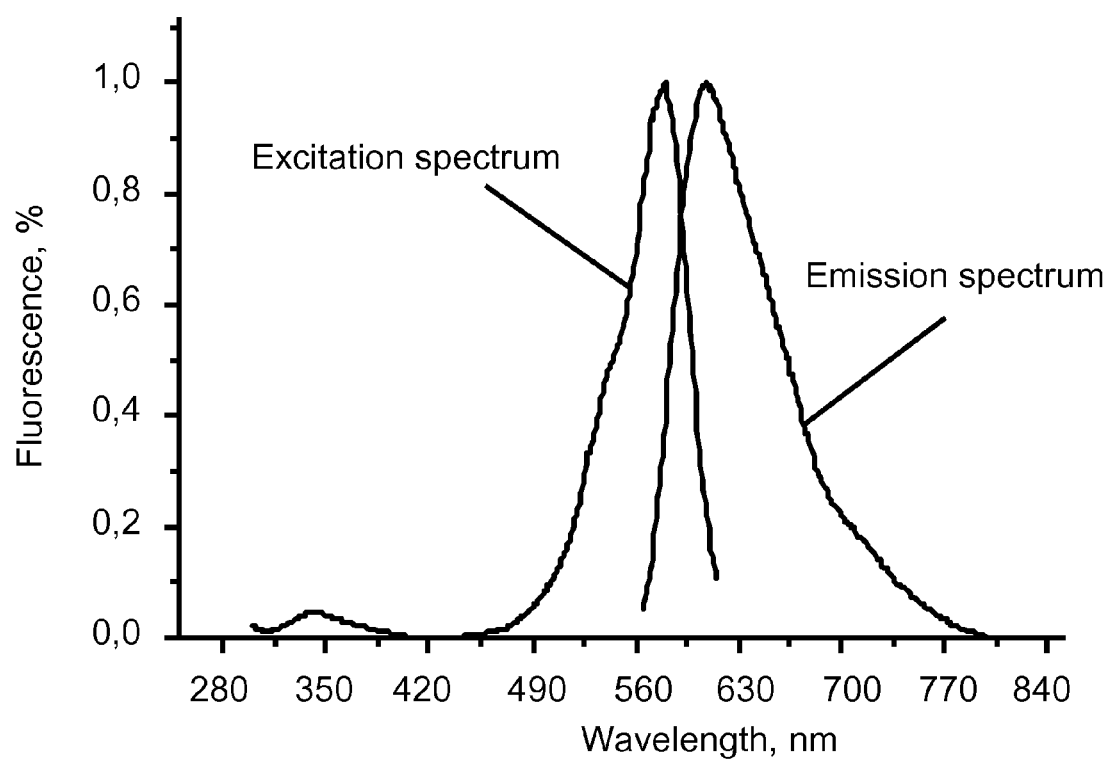
FIG. 4 illustrates normalized excitation and emission spectra of the mKate2.7C fluorescent protein.

Combining the aforementioned mutations yield a protein named mKate2.7C (SEQ ID NO:29, SEQ ID NO:30), which contained the following 9 amino acid substitutions not contained in mKate 2.5: H11P (enhances folding), K68R (enhances pH stability), N72K (enhances folding), Q75P (enhances folding), I122V (enhances folding), L148M (enhances folding), K186T (enhances folding), R198H (enhances pH stability), and N208D (enhances folding). mKate2.7C demonstrated enhanced brightness after overnight expression at 37° C. compared to mKate2.5, indicating its faster folding and maturation at 37° C. mKate2.7C is characterized by desirable high pH-stability, with pKa=4.5. Excitation/emission spectra are blue-shifted compared to mKate2.5, and are peaked at 579/608 nm (FIG. 4). mKate2.7C has relatively high brightness with fluorescence quantum yield=0.18 and molar extinction coefficient=125,000 cm$^{-1}$ mol$^{-1}$, maturation rate—approximately 100 min maturation half-time at 37° C., and photostability, comparable to the photostability of the previously reported monomeric red FPs, TagRFP and mKate2, both upon widefield and confocal excitation. mKate2.7C as well as mKate2.5 displays purely monomeric behaviour on FPLC analysis at high concentrations (>1 mg/ml, FIG. 2).

Example 9

Generation of Photoactivatable Red Fluorescent Proteins on the Basis of mKate2.7C The nucleic acid encoding mKate2.7C protein was obtained as described in Example 8 and subjected to alternative site-directed mutagenesis S144A/G, C159A/G, resulting in four alternative mutant variants. These mutations provide structural space for the cis-trans isomerization of the chromophore and thus result in photoactivatable variants (Chudakov et al., J Biol Chem. 2003 Feb. 28; 278(9):7215-9.). The obtained mutant variants were transformed in *E. coli* (XL1-blue strain). *E. coli* colonies expressing mutant protein variants were grown at 37° C. overnight and screened for the photoactivatable variants using fluorescent microscope. One of the variants was selected which demonstrated bright red fluorescence that could be reversibly quenched by intense green light (545-580 nm) irradiation. After 5 min in the dark the protein reversed back to the bright red fluorescent state. A 4-fold or greater contrast was observed between the two states at least 4-fold. Sequence analysis revealed that the protein, designated as mKate2.7C-PA1 (SEQ ID NO:32, SEQ ID NO:33), contains substitutions S144A and C159A.

The nucleic acid encoding mKate2.7C protein was also subjected to site-directed mutagenesis, substituting S144H and R68K. These mutations are characteristic for the homologous photoactivatable protein KFP-HC (Zhang et al., Bioorganic chemistry, Russian. 2010, 36 (2):187-192). The obtained mutant variant was transformed in *E. coli* (XL1-blue strain). *E. coli* colonies expressing mutant variant were grown at 37° C. overnight and recombinant protein was purified via a metal-affinity resin TALON (Clontech). This mutant variant, designated as mKate2.7C-PA2 (SEQ ID NO:34, SEQ ID NO:35), demonstrated bright red fluorescence that could be quenched by intense green light (545-580 nm) irradiation and kindled back by blue (460-490 nm) light irradiation in reversible manner. The contrast between the two states comprise at least 8-fold.

Example 10

Expression of mKate2.5 and mKate2.7C in Mammalian Cells

Nucleic acids encoding mKate2.5 and mKate2.7C were obtained as described in the Examples 3 and 8, respectively, and operatively cloned into the pTurboGFP-N vector (Evrogen) in place of TurboGFP sequence under the control of CMV promoter. HeLa cells transient transfected with these constructs became brightly fluorescent after 16 h of incubation at 37° C.

Nucleic acids encoding mKate2.5 and mKate2.7C were cloned into pmKate2-f-mem (Evrogen), pTagRFP-Cx43 (Evrogen), pmKate2-tubulin (Evrogen), and pTagRFP-vinculin (Evrogen) vectors in place of mKate2 and TagRFP sequences. Fusion proteins were then generated in which mKate2.5 or mKate2.7C were fused to either the farnesylation signal peptide (the 20 amino acid farnesylation signal from c-Ha-Ras that targeted the protein to plasma membrane (Aronheim et al., Cell. 1994; 78 (6):949-61; Hancock et al., EMBO J. 1991; 10 (3):641-6) or connexin-43, alpha-tubulin, or vinculin. Upon transient transfection of HeLa cells, both mKate2.5 and mKate2.7C demonstrate excellent performance in fusion with these peptides and polypeptides.

TABLE 1

Summary of mutants of particular interest. Positions correspond to positions in the mKate2 sequence. Amino acids that follow the position number are the amino acid that is substituted in at that position.

| Name of protein | Nucleic Acid Sequence | Protein Sequence | Mutations |
| --- | --- | --- | --- |
| mKate2 | SEQ ID NO: 1 | SEQ ID NO: 2 | |
| mKate2M1 | SEQ ID NO: 3 | SEQ ID NO: 4 | 158A, 159C, 176E, 195N, C' substitution |
| pH-Redder-0.1 | SEQ ID NO: 5 | SEQ ID NO: 6 | 46V, 136R, 147M, 159S, 176E |
| mKate2M1sens1 | SEQ ID NO: 7 | SEQ ID NO: 8 | 158A, 159G, 176E, 195N, C' substitution |
| mKate2M1fold1 | SEQ ID NO: 9 | SEQ ID NO: 10 | 74P, 158A, 159C, 176E, 195N, 208N, C' substitution |
| mKate2M1fold2 | SEQ ID NO: 11 | SEQ ID NO: 12 | 74G, 158A, 159C, 176E, 195N, 208S, C' substitution |
| mKate2M1stab1 | SEQ ID NO: 13 | SEQ ID NO: 14 | 158A, 159V, 176E, 195N, C' substitution |
| mKate2M1stab2 | SEQ ID NO: 15 | SEQ ID NO: 16 | 158A, 159N, 176E, 195N, C' substitution |
| mKate2M1farred1 | SEQ ID NO: 17 | SEQ ID NO: 18 | 42L, 158A, 159C, 176E, 195N, C' substitution |
| mKate2M1farred2 | SEQ ID NO: 19 | SEQ ID NO: 20 | 42V, 158A, 159C, 176E, 195N, C' substitution |
| mKate2M1farred3 | SEQ ID NO: 21 | SEQ ID NO: 22 | 42V, Q107N, 158A, 159C, 176E, 195N, C' substitution |
| mKate2M1orange1 | SEQ ID NO: 23 | SEQ ID NO: 24 | 144C, 158A, 159T, 176E, 195N, 198Y, C' substitution |
| mKate2M1photo1 | SEQ ID NO: 25 | SEQ ID NO: 26 | 144H, 158A, 159C, 176E, 195N, 198H, C' substitution |
| mKate2.5 | SEQ ID NO: 27 | SEQ ID NO: 28 | 46V, 74P, 129A, 158A, 159C, 176E, 195N, 208N, C' substitution |
| mKate2.7C | SEQ ID NO: 29 | SEQ ID NO: 30 | 11P, 46V, 68R, 72K, 74P, 75P, 122V, 129A, 148M, 158A, 159C, 176E, 186T, 195N, 198H, 208D, C' substitution |
| mKate2.7C-PA1 | SEQ ID NO: 32 | SEQ ID NO: 33 | 11P, 46V, 68R, 72K, 74P, 75P, 122V, 129A, 144A, 148M, 158A, 176E, 186T, 195N, 198H, 208D, C' substitution |
| mKate2.7C-PA2 | SEQ ID NO: 34 | SEQ ID NO: 35 | 11P, 46V, 72K, 74P, 75P, 122V, 129A, 144H, 148M, 158A, 159C, 176E, 186T, 195N, 198H, 208D, C' substitution |
| mKate2.6 | SEQ ID NO: 38 | SEQ ID NO: 39 | 46V, 68R, 74P, 129A, 158A, 159C, 176E, 195N, 198H, 208N, C' substitution |

All publications and patent applications cited in this specification are incorporated by reference herein as if each individual publication or patent application were specifically and individually indicated to be incorporated by reference. The citation of any publication is to provide context and understanding of the present invention and should not be construed as an admission that any such publication is prior art.

What is claimed:

1. A nucleic acid present in other than its natural environment, wherein the nucleic acid encodes a fluorescent protein that emits fluorescence, comprises a GFP-like domain, and has a substantially reduced tendency to form dimers relative to SEQ ID NO:2, wherein the protein comprises at least one substitution at a position corresponding to a position in SEQ ID NO:2 selected from the group consisting of position 158, 176, 195, and 225.

2. The nucleic acid according to claim 1, wherein the substitution is selected from the group consisting of R158A, R158S, R158D, R158N, R158G, K176E, K176N, K176D, K176S; Y195N, Y195D, Y195V, Y195A, Y195T, Y195E, Y195S, Y195C, Y195G; L225G, L225E, L225A, L225T, and L225N corresponding to SEQ ID NO:2.

3. The nucleic acid according to claim 2, wherein the substitution is selected from the group consisting of R158A, K176E, Y195N, and L225G corresponding to SEQ ID NO:2.

4. The nucleic acid according to claim 3, wherein the substitution is the substitution K176E corresponding to SEQ ID NO:2.

5. The nucleic acid according to claim 4, further comprising substitutions R158A and Y195N corresponding to SEQ ID NO:2.

6. The nucleic acid according to claim 1, further comprising a substitution of C-terminal residues corresponding to residues 223-232 of SEQ ID NO:2.

7. The nucleic acid according to claim 6, wherein the C-terminal residues are substituted with SEQ ID NO:31.

8. The nucleic acid according to claim 1, wherein the protein has the amino acid sequence of SEQ ID NOS: 2, 4, 6, 8, 10, 12, 14, 16, 18, 20, 24, 26, 30, 33, 35 or 39.

9. A vector comprising the nucleic acid of claim 1.

10. An expression cassette comprising:
(a) the nucleic acid according to claim 1; and
(a) a transcriptional initiation region that is operatively linked to the nucleic acid in (a) and is functional in an expression host; and (c) a transcriptional termination region that is operatively connected to the nucleic acid in (a) and is functional in the expression host.

11. A host cell or progeny thereof, comprising the expression cassette according to claim 10 as part of an extrachromosomal element or integrated into the genome of a host cell as a result of introduction of the expression cassette into the host cell.

12. A transgenic cell, or progeny thereof, comprising the nucleic acid according to claim 1.

13. A fluorescent protein or mutant thereof, wherein the protein emits fluorescence, has a substantially reduced tendency to form dimers as compared with mKate2 (SEQ ID NO:2), and comprises a sequence that differs from the amino acid sequence of full length SEQ ID NO:2 by at least one amino acid substitution, wherein that substitution is at a position corresponding to a position in SEQ ID NO:2 selected from the group consisting of 158, 176, 195, and 225.

14. A fluorescent protein according to claim 13, wherein the substitution is selected from the group consisting of R158A, R158S, R158D, R158N, R158G, K176E, K176N, K176D, K176S; Y195N, Y195D, Y195V, Y195A, Y195T, Y195E, Y195S, Y195C, Y195G; L225G, L225E, L225A, L225T, and L225N corresponding to SEQ ID NO:2.

15. The fluorescent protein according to claim 14, wherein the substitution is selected from the group consisting of R158A, K176E, Y195N, and L225G corresponding to SEQ ID NO:2.

16. A kit comprising the nucleic acid according to claim 1.

17. An antibody that specifically bind to the fluorescent protein of claim 13.

* * * * *